(12) United States Patent
Fu

(10) Patent No.: US 10,668,111 B2
(45) Date of Patent: Jun. 2, 2020

(54) USE OF UMBILICAL MESENCHYMAL STEM CELLS FOR TREATING PULMONARY FIBROSIS

(71) Applicants: NATIONAL YANG MING UNIVERSITY, Taipei (TW); Yu-Show Fu, Taipei (TW)

(72) Inventor: Yu-Show Fu, Taipei (TW)

(73) Assignees: NATIONAL YANG MING UNIVERSITY, Taipei (TW); Yu-Show Fu, Taipei (TW)

(*) Notice: Subject to any disclaimer, the term of this patent is extended or adjusted under 35 U.S.C. 154(b) by 0 days.

(21) Appl. No.: 15/874,674

(22) Filed: Jan. 18, 2018

(65) Prior Publication Data
US 2018/0271917 A1 Sep. 27, 2018

(30) Foreign Application Priority Data
Jan. 18, 2017 (TW) .............................. 106101701 A

(51) Int. Cl.
| | | |
|---|---|---|
| A61K 35/51 | (2015.01) | |
| C12N 5/073 | (2010.01) | |
| A61P 11/00 | (2006.01) | |
| A61K 9/00 | (2006.01) | |

(52) U.S. Cl.
CPC ............ *A61K 35/51* (2013.01); *A61K 9/0019* (2013.01); *A61P 11/00* (2018.01)

(58) Field of Classification Search
CPC .... C12N 5/0605; A61K 35/51; A61K 9/0019; A61P 11/00
See application file for complete search history.

(56) References Cited

U.S. PATENT DOCUMENTS

| | | | | |
|---|---|---|---|---|
| 2008/0311088 A1* | 12/2008 | Chang | .................... | A61K 35/28 424/93.7 |
| 2009/0232781 A1* | 9/2009 | Fu | ......................... | A61K 35/44 424/93.7 |

OTHER PUBLICATIONS

Nagannura-Inoue et al., "Umbilical cord derived mesenchymal stem cells: Their advantages and potential clinical utility", WJSC, Apr. 2014, 6(2): 195-202 (Year: 2014).*
Mennan et al., "Isolation and Characterization of Mesenchymal Stem Cells from Different Regions of the Human Umbilical Cord", Biomedical Research International, vol. 2013, Article ID 916136, p. 1-8 (Year: 2013).*
Makarev et al., "Common pathway signature in lung and liver fibrosis", Cell Cycle, 2016, vol. 15, No. 13, 1667-1673 (Year: 2016).*

* cited by examiner

*Primary Examiner* — Ruth A Davis
(74) *Attorney, Agent, or Firm* — Birch, Stewart, Kolasch & Birch, LLP

(57) ABSTRACT

The present invention relates to treatment of pulmonary fibrosis with umbilical mesenchymal stem cell.

18 Claims, 15 Drawing Sheets

Specification includes a Sequence Listing.

BLM+HUMSCs (LD) D49

BLM+HUMSCs (HD) D49

SEQUENCE LISTING

```
<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: Synthetic primer:  Human SP-D

<400> SEQUENCE: 1
aggagcaaag ggagaaagtg g                                          21

<210> SEQ ID NO 2
<211> LENGTH: 20
<212> TYPE: DNA
<213> ORGANISM: Artificial Sequence
<220> FEATURE:
<223> OTHER INFORMATION: Synthetic primer:  Human SP-D

<400> SEQUENCE: 2
gctgtgcctc cgtaaatggt                                            20

<210> SEQ ID NO 3
<211> LENGTH: 21
<212> TYPE: DNA
<213> ORGANISM: Artificial Sequence
<220> FEATURE:
<223> OTHER INFORMATION: Synthetic primer:  Human PECAM1

<400> SEQUENCE: 3
tcaagaaaag caacacagtc c                                          21

<210> SEQ ID NO 4
<211> LENGTH: 20
<212> TYPE: DNA
<213> ORGANISM: Artificial Sequence
<220> FEATURE:
<223> OTHER INFORMATION: Synthetic primer:  Human PECAM1

<400> SEQUENCE: 4
actccgatga taaccactgc                                            20

<210> SEQ ID NO 5
<211> LENGTH: 18
<212> TYPE: DNA
<213> ORGANISM: Artificial Sequence
<220> FEATURE:
<223> OTHER INFORMATION: Synthetic primer:  Human GAPDH
```

```
<400> SEQUENCE: 5
tcctccacct ttgacgct                                                    18

<210> SEQ ID NO 6
<211> LENGTH: 20
<212> TYPE: DNA
<213> ORGANISM: Artificial Sequence
<220> FEATURE:
<223> OTHER INFORMATION: Synthetic primer:  Human GAPDH

<400> SEQUENCE: 6
tcttcctctt gtgctcttgc                                                  20

<210> SEQ ID NO 7
<211> LENGTH: 22
<212> TYPE: DNA
<213> ORGANISM: Artificial Sequence
<220> FEATURE:
<223> OTHER INFORMATION: Synthetic primer:  Rat GAPDH

<400> SEQUENCE: 7
ctctacccac ggcaagttca ac                                               22

<210> SEQ ID NO 8
<211> LENGTH: 23
<212> TYPE: DNA
<213> ORGANISM: Artificial Sequence
<220> FEATURE:
<223> OTHER INFORMATION: Synthetic primer:  Rat GAPDH

<400> SEQUENCE: 8
ggtgaagacg ccagtagact cca                                              23

<210> SEQ ID NO 9
<211> LENGTH: 24
<212> TYPE: DNA
<213> ORGANISM: Artificial Sequence
<220> FEATURE:
<223> OTHER INFORMATION: Synthetic primer:  Human/Rat beta-actin

<400> SEQUENCE: 9
ttgtaaccaa ctgggacgat atgg                                             24

<210> SEQ ID NO 10
<211> LENGTH: 24
<212> TYPE: DNA
<213> ORGANISM: Artificial Sequence
<220> FEATURE:
<223> OTHER INFORMATION: Synthetic primer:  Human/Rat beta-actin

<400> SEQUENCE: 10
gatcttgatc ttcatggtgc tagg                                             24
```

USE OF UMBILICAL MESENCHYMAL STEM CELLS FOR TREATING PULMONARY FIBROSIS

REFERENCE TO SEQUENCE LISTING SUBMITTED VIA EFS-WEB

This application includes an electronically submitted sequence listing in .txt format. The .txt file contains a sequence listing entitled "2018-06-13 5992-0203PUS1_ST25.txt" created on May 8, 2018 Jun. 13, 2018 and is 2,380 bytes in size. The sequence listing contained in this .txt file is part of the specification and is hereby incorporated by reference herein in its entirety.

RELATED APPLICATION

This application claims priority to Taiwan Patent Application No. 106101701, filed on Jan. 18, 2017, the content of which is hereby incorporated by reference in its entirety.

TECHNOLOGY FIELD

The present invention relates to use of umbilical mesenchymal stem cell for the treatment of pulmonary fibrosis.

BACKGROUND OF THE INVENTION

Lung tissues damage can be caused by numerous factors such as smoking, aging, air pollution, bacteria, viruses, free radicals, radiation, and chemotherapeutic agents, as well as by hereditary factors. When a lung is damaged, the number of functional alveoli decrease and the alveolar compartments are gradually replaced by fibrotic tissues, causing pulmonary fibrosis. Pulmonary fibrosis is irreversible and causes progressive deterioration in lung functionality. To date, no effective therapy exists for pulmonary fibrosis. Critically, the mortality rate for pulmonary fibrosis is increasing every year.

The lung alveolar epithelium covers the internal surface area of the lung and is composed of two morphological and functional distinct types of cells: type I alveolar epithelial cells (AEC1s) and type II alveolar epithelial cells (AEC2s). When alveoli are injured, AEC2s proliferate and transdifferentiate into AEC1s to repair them facilitate restoration of lung epithelium (1-3). Nevertheless, when severe injuries cause the extensive death of AEC1s, the damaged areas secrete numerous inflammatory cytokines, such as transforming growth factor beta (TGF-β). TGF-β attracts numerous immune cells infiltrating the lesion, which triggers further inflammatory responses. The inflammatory signals enhances the epithelial-mesenchymal transition (EMT) of AEC2s, indicating that numerous AEC2s transform into myofibroblasts. Activated myofibroblasts not only proliferate and express α-smooth muscle actin (α-SMA) but also produce and release the extracellular matrix (ECM). The deposition of ECM components in the interstitial and alveolar space is a hallmark of pulmonary fibrosis. The thickening of alveolar septal walls results in a more severe and irreversible lung consolidation, which impedes the lung's ability to air exchange, leading to a deterioration in pulmonary function (4-10).

Some researchers have studies the effects of stem cells from various origins, such as adipose tissue mesenchymal stem cells (MSCs) (20, 21), bone marrow MSCs (14, 22), and human umbilical mesenchymal stem cells from Wharton's jelly (HUMSCs) (23, 24), in inhibiting inflammatory responses or acute injuries in the lung. However, in most relevant studies, stem cells were transplanted either immediately or one day after lung damage, thus focussing on the effect of stem cells in treating acute injuries or in preventing inflammation in the lung and thus preventing formation of pulmonary fibrosis. Further, it has been reported that bone marrow MSCs injected into the lung immediately after irradiation could differentiate into functional lung cells and thus be useful in treatment of lung injury while those injected at later stage after irradiation would be involved in fibrosis development (25).

In clinical practice, most patients attend clinics for respiratory problems are not in the early stage but usually when pulmonary fibrosis has already developed. There is a need to provide a therapeutically effective approach in treating a fibrosis condition in the lung, particularly reversing the status of pulmonary fibrosis.

BRIEF SUMMARY OF THE INVENTION

The present invention is based on the unexpected findings that delivery of umbilical mesenchymal stem cells (UMSCs) into animal models of pulmonary fibrosis is effective in reducing the fibrosis condition(s) and recovering lung functionality in the animals.

Therefore, the present invention provides a method for treating a fibrosis condition of the lung in a subject in need, comprising administering to the subject an effective amount of umbilical mesenchymal stem cells (UMSCs) to the subject. Also provided is use of UMSCs for manufacturing a medicament for treating a fibrosis condition of the lung in a subject in need. A pharmaceutical composition comprising UMSCs for use in treating a fibrosis condition of the lung in a subject in need is provided.

In some embodiments, the UMSCs are obtained from Wharton's Jelly.

In some embodiments, the UMSCs are human umbilical mesenchymal stem cells (HUMSCs).

In some embodiments, the method is effective in reducing or alleviating one or more fibrosis conditions of the lung, selected from the group consisting of an elevated level of collagen deposition in the lung, an elevated level of cell infiltration in the lung, an elevated level of lung density and an elevated level of activation of fibroblast in the lung, as compared with a normal level.

In some embodiments, the method is effective in increasing a reduced level of lung volume, a reduced level of lung air space, and/or a reduced level of number of alveoli, as compared with a normal level.

In some embodiments, the method is effective in improving a decreased level of oxygen saturation in the blood, alleviating an increased level of respiratory rate and/or recovering shrinking of the lung.

In some embodiments, the method is effective in promoting degradation of fibrotic tissues that have occurred in the lung.

In some embodiments, the method is effective in promoting restoration of lung epithelium.

In some embodiments, the UMSCs are administered via injection.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

Western blot images (upper part) represent the contents of α-SMA in the rats' left lungs and the quantitative results (lower part) of α-SMA from Western blotting is provided. The results indicated that activated fibroblasts significantly increased from Day 7 to 49. The activated fibroblasts significantly decreased after the transplantation of high doses of HUMSCs. *: $p<0.05$ versus the Normal group.

Figure 11:
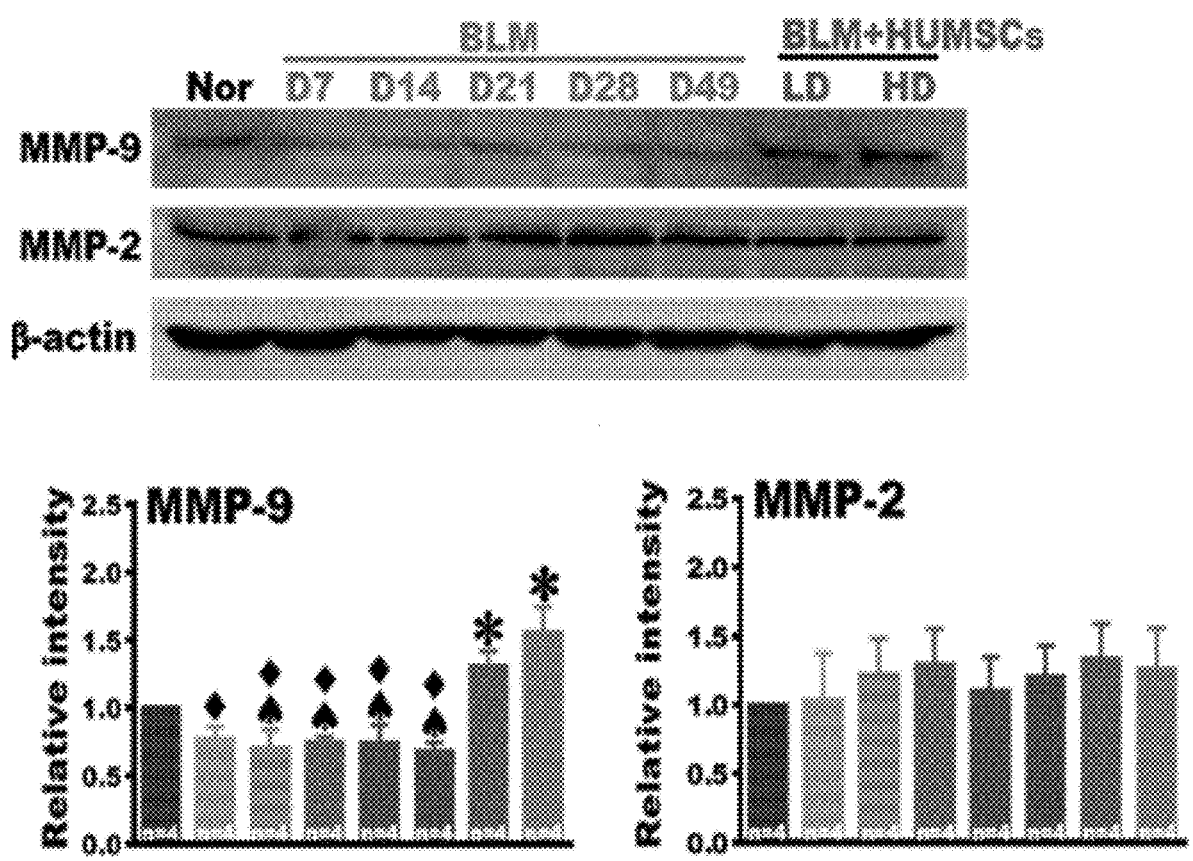

FIG. 11 shows that HUMSCs stimulated collagen degradation in the left lungs of rats with pulmonary fibrosis. The contents of MMP-9 and MMP-2 in the rats' left lungs were detected through Western blotting (upper part). The quantitative results (lower part) indicate that MMP-9 significantly increased following the transplantation of HUMSCs, whereas no significant alteration was found for MMP-2. *: $p<0.05$ versus the Normal group.

Figure 12:
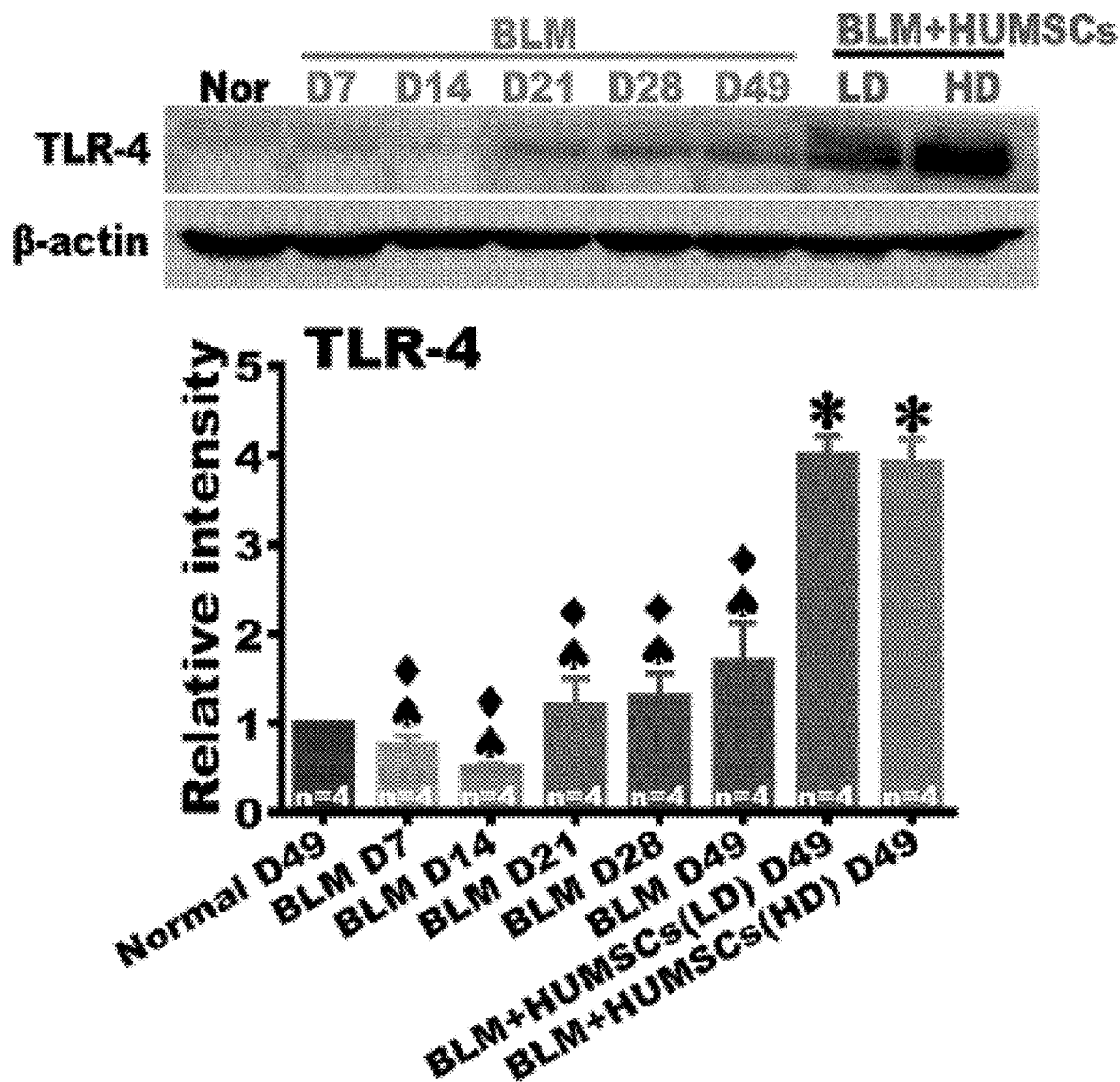

FIG. 12 shows that HUMSCs enhanced TLR-4 expression to facilitate recovery of alveolar epithelial cells in the left lungs of rats with pulmonary fibrosis. Toll-like receptor 4 (TLR-4) was detected through Western blotting (upper part). The quantitative results (lower part) indicate that transplantation of HUMSCs enhances the synthesis of TLR-4 in the left lungs of rats with pulmonary fibrosis and thus promotes the restoration of alveolar epithelial cells. *: $p<0.05$ versus the Normal group. ▲: $p<0.05$ versus the BLM+HUMSCs (LD) group. ♦: $p<0.05$ versus the BLM+HUMSCs (HD) group.

Figure 13A:
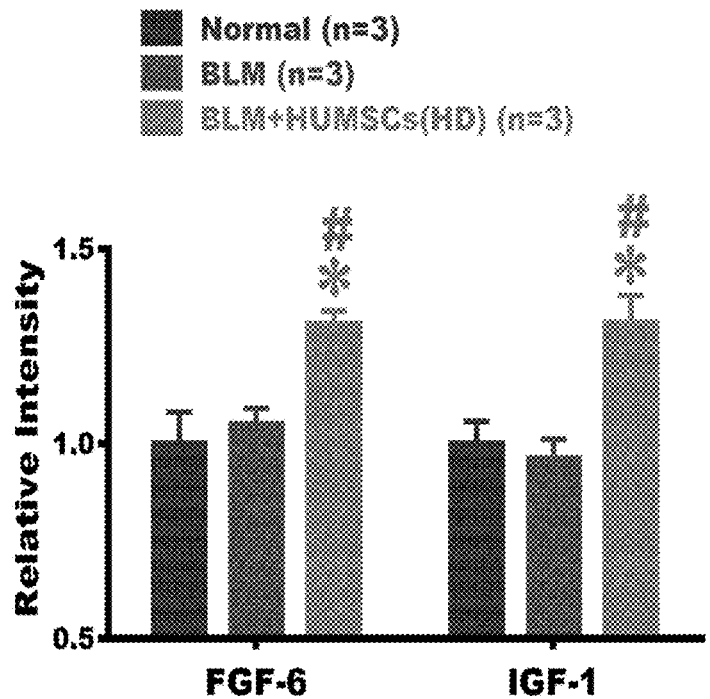
Figure 13B:
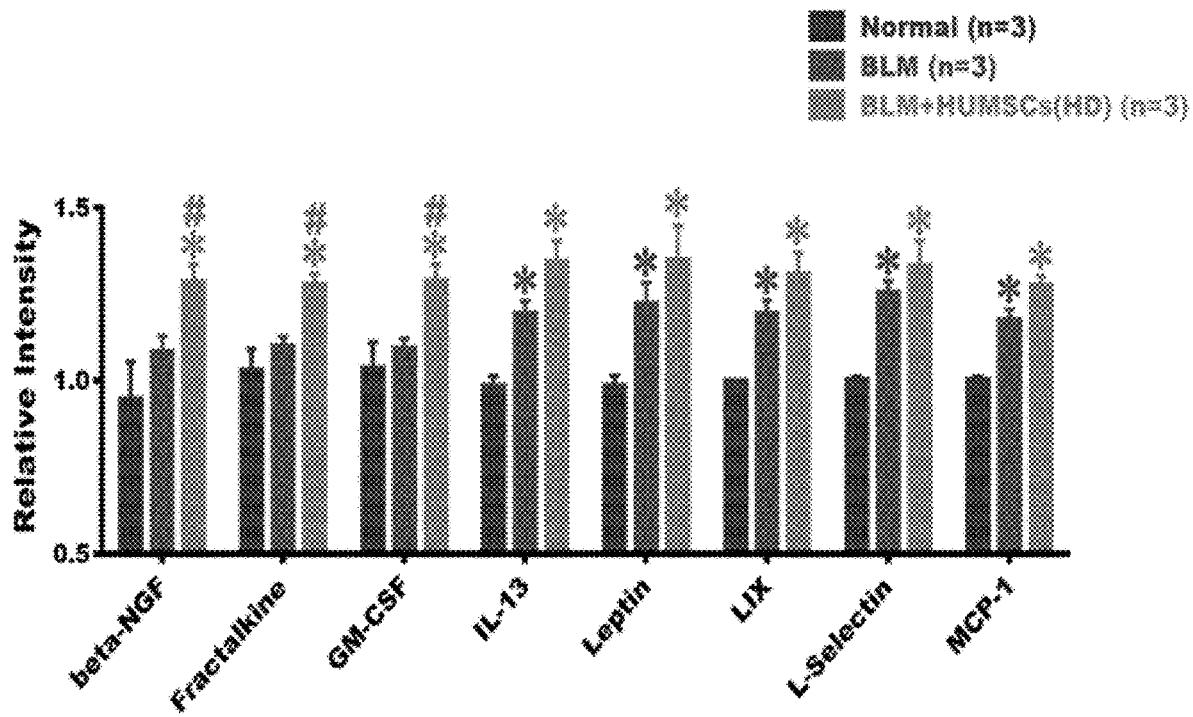

FIGS. 13A and 13B include charts showing that HUMSCs secreted cytokines that assisted in repairing the lungs of rats with pulmonary fibrosis. Left lung samples from the Normal, BLM, and BLM+HUMSCs (HD) groups on Day 49 were subjected to Human Cytokine Antibody Array analysis. The results suggested that the transplantation of HUMSCs increased human fibroblast growth factor (FGF)-6 and insulin-like growth factor (IGF)-1 concentrations in rats with pulmonary fibrosis (FIG. 13A). Corresponding cytokines on the Human Cytokine Array membrane Analyses were conducted using Rat Cytokine Antibody Array. The results indicated that the transplantation of HUMSCs stimulated rats with pulmonary fibrosis to produce higher amounts of β-nerve growth factor (NGF), fractalkine, and granulocyte-macrophage colony-stimulating factor (GM-CSF) in their left lungs (FIG. 12B). BLM damage resulted in elevated concentrations of IL-13, leptin, LIX, L-Selectin, and MCP-1 (FIG. 13B). *: $p<0.05$ versus the Normal group. #: $p<0.05$ versus the BLM group.

DETAILED DESCRIPTION OF THE INVENTION

Unless defined otherwise, all technical and scientific terms used herein have the same meanings as is commonly understood by one of skill in the art to which this invention belongs.

As used herein, the articles "a" and "an" refer to one or more than one (i.e., at least one) of the grammatical object of the article. By way of example, "an element" means one element or more than one element.

The term "comprise" or "comprising" is generally used in the sense of include/including which means permitting the presence of one or more features, ingredients or components. The term "comprise" or "comprising" encompasses the term "consists" or "consisting of."

As used herein, "umbilical mesenchymal stem cells (UMSCs)" refer to stem cells in the mammalian umbilical cord, preferably the mesenchymal tissue therein, including unpurified cell cultures or purified cells. UMSCs are multipotent and can differentiate into a variety of cell types, such as osteoblasts, chondrocytes, myocytes, adipocytes and neuron-like cells. UMSCs are of many advantages. Umbilical cord, considered medical waste after birth, is easy available with no moral concerns, and UMSCs can be obtained by simple treatment from the source and the cells are numerous and capable of rapid expansion in culture. In particular, some studies have indicated that human UMSCs are immunologically compatible and therefore suitable for allogeneic transplantation.

UMSCs suitable for use in the present invention may be derived from umbilical cord "Wharton's jelly," which is also known as inter-laminar jelly, a mucous-connective tissue substance found in the umbilical cord. UMSCs as described herein may be obtained in a number of ways. For example, they may be derived from umbilical tissue. The umbilical tissue may be processed, such as by dissection, mincing, washing, enzymatic digesting, or any combination thereof. The term "UMSCs" encompasses not only the stem cells isolated directly from the mesenchymal tissue in the umbilical cord, but also stem cells cultivated in vitro from the stem cells isolated directly from the mesenchymal tissue in umbilical cord. The cells may be cultured in any suitable medium, such as Dulbecco's Modified Eagle Medium (DMEM), which may be supplemented with any suitable supplement, such as fetal bovine serum (FBS). The cells may be confirmed or selected based on their characteristics known in this art, for example, their ability to adhere to a substrate e.g. the vessel's surface and/or a particular profile of cell surface marker(s) e.g. positive expression of CD105, CD44, CD90 and/or CD73 and/or negative expression of HLA, CD34, CD14, CD19, and/or CD45. Preferably, the UMSCs are human umbilical mesenchymal stem cells (HUMSCs). Methods for isolating UMSCs from umbilical cord, in vitro cell cultivation/expansion and cell characterization are known and available in this art, as described in, for example, U.S. Patent Application Publication No. 20080305148 and 20150125950.

As used herein, "pulmonary fibrosis (PF)" or a fibrosis condition in the lung is a pulmonary disease or condition that involves the formation of scar or fibrous connective tissue of the lung tissue. In normal adult lungs, over about 25% (w/w) of the lung are connective tissues, mainly composed of extracellular matrix (ECM) such as collagen, elastin, proteoglycans, and glycoproteins. In general, when lungs are damaged, lung fibroblasts are activated to produce ECM. The ECM can be degraded by proteases e.g. certain matrix metalloproteases (MMPs). The accumulation of excess ECM causes thickening of the walls and leads to breathing problems. Lung tissue damages also induce inflammatory responses, increasing cell infiltration in the lung. Other features of fibrosis in the lung include increase of lung density (e.g. total cell count (TCC) in bronchoalveolar lavage fluid (BALF)), reduction of lung volume, lung air space and number of alveoli, and shrinking of the lung. Patients with a fibrosis condition in the lung may exhibit rapid respiratory rate and poor gas exchange. Other common symptoms include, hacking cough, fatigue and weakness, discomfort in the chest, loss of appetite, and weight loss. Conventional tests are available for identifying a patient suffering from a fibrosis condition in the lung, for example, chest X-Ray, high-resolution computerized tomography (HRCT), magnetic resonance imaging (MRI), pulmonary function tests, pulse oximetry, arterial blood gas (ABG) determination, bronchoscopy, bronchoalveolar Lavage (BAL), surgical lung biopsy, exercise testing, esophogram, and echocardiogram (ECHO).

In clinical, a patient diagnosed with pulmonary fibrosis (PF) can be idiopathic or non-idioppahic (secondary). When there is no known cause for the development of pulmonary fibrosis, such fibrosis is called idioppahi pulmonary fibrosis (IPF). If there is a clear association of the fibrosis with another disorder or the fibrosis/scarring in the lung is a side effect from a specific medication or an exposure to an agent known to cause fibrosis in the lung, then such fibrosis referred to as non-idiopathic pulmonary fibrosis. For example, pulmonary fibrosis clearly associated with another disease, such as scleroderma or rheumatoid arthritis, can be considered pulmonary fibrosis secondary to scleroderma or secondary to rheumatoid arthritis. Some other examples of factors that are considered contributing to pulmonary fibrosis include cigarette smoking, exposure to environmental contaminants or dusts, viral or bacterial lung infections, particular medicines, such as some antibiotics, chemotherapeutic agents, or therapeutic radiation, and genetic predisposition.

As used herein, a reduced or elevated level of an index or symptom related to a fibrosis condition in the lung as described herein is with reference to a control (or normal) level thereof. As used herein, the term "normal level" or "control level" is meant to describe a value within an acceptable range of values that one of ordinary skill in the art and/or a medical professional e.g. a doctor would expect a healthy individual or population of similar physical characteristics and medical history to have. For example, an elevated level means a level above a control (or normal) level by 5%, 10%, 20%, 30%, 50%, 70%, 90%, 100%, 200%, 300%, 500% or more compared to a control (or normal) level; and an reduced level means a level below a control (or normal) level by 5%, 10%, 20%, 30%, 50%, 70%, 90%, 100%, 200%, 300%, 500% or more compared to a control (or normal) level.

The term "a subject in need of the method of treatment" as used herein, is intended to mean a human or non-human animal that is in need of treatment of pulmonary fibrosis or a fibrosis condition in the lung. In particular, a subject in need of the method of treatment is an individual suffering from one or more fibrosis conditions in the lung.

In some embodiments, a subject in need of the method of treatment of the present invention exhibits one or more conditions of: an elevated level of collagen deposition in the lung, an elevated level of cell infiltration in the lung, an elevated level of lung density and/or an elevated level of activation of fibroblast in the lung, as compared with a normal level.

In some embodiments, a subject in need of the method of treatment of the present invention exhibits one or more conditions of: a reduced level of lung volume, a reduced level of lung air space, a reduced level of number of alveoli and shrinking of the lung, as compared with a normal level.

In some embodiments, a subject in need of the method of treatment of the present invention exhibits a decreased level of blood oxygen saturation and/or an increased level of respiratory rate, due to damaged functionality of the lung, as compared with a normal level.

In certain embodiments, a subject in need of the method of treatment of the present invention is a patient diagnosed with pulmonary fibrosis (PF).

The term "individual" or "subject" used herein includes human and non-human animals such as companion animals (such as dogs, cats and the like), farm animals (such as cows, sheep, pigs, horses and the like), or laboratory animals (such as rats, mice, guinea pigs and the like).

The term "treating" as used herein refers to the application or administration of a composition including one or more active agents to a subject afflicted with a disorder, a symptom or conditions of the disorder, or a progression of the disorder, with the purpose to cure, heal, alleviate, relieve, alter, remedy, ameliorate, improve, or affect the disorder, the symptoms or conditions of the disorder, the disabilities induced by the disorder, or the progression of the disorder. Specifically, as used herein, treating pulmonary fibrosis or a fibrosis condition of the lung includes aiding recovery or reversion from the fibrosis toward a normal state, completely or partially.

The term "therapeutically effective amount" used herein refers to the amount of an active ingredient to confer a desired therapeutic or biological effect in a treated subject. For example, an effective amount for treating a fibrosis condition of the lung may be an amount of UMSCs sufficient to cause a certain degree of recovery (or reversion) from the disease state toward a normal level, completely or partially.

In some embodiments, a therapeutically effective amount of UMSCs is an amount sufficient to cause 5%, 5%, 10%, 20%, 30%, 50%, 70%, 90%, 100%, 200%, 300% or 500% or more decrease in ECM (e.g. collagen) deposition in the lung, cell infiltration in the lung, lung density and/or activation of fibroblast in the lung, relative to the counterpart level prior to administration of UMSCs.

In some embodiments, a therapeutically effective amount of UMSCs is an amount sufficient to cause 5%, 5%, 10%, 20%, 30%, 50%, 70%, 90%, 100%, 200%, 300% or 500% or more increase in lung volume, lung air space, number of alveoli, and/or lung functionality relative to the counterpart level prior to administration of UMSCs.

In some embodiments, a therapeutically effective amount of UMSCs is an amount sufficient to cause an increased degree of degradation of ECM (e.g. collagen) and/or restoration of lung epithelium, relative to the counterpart level prior to administration of UMSCs. Specifically, degradation of ECM can be caused by activation of some certain matrix metalloproteases (MMPs) e.g. MMP9. In addition, restoration of lung epithelium may involve proliferation of type II alveolar epithelial cells (AEC2s) and transdifferentiate into type I alveolar epithelial cells (AEC1s).

The therapeutically effective amount may change depending on various reasons, such as administration route and frequency, body weight and species of the individual receiving said pharmaceutical, and purpose of administration. Persons skilled in the art may determine the dosage in each case based on the disclosure herein, established methods, and their own experience. For example, in certain embodiments, the UMSCs are administered in an amount of at least $10^4$, $10^5$, $10^6$, $10^7$, $10^8$, $10^9$ or more cells per administration.

According to the present invention, the UMSCs may be administered by a variety of procedures as known in the art. The cells may be administered systemically, such as by intravenous, intraarterial, nasal, or intraperitoneal administration, via injection, for example. The cells may be from a spectrum of sources including autologous, allogeneic, or xenogeneic.

In particular, to perform the method of the invention, the UMSCs may be directly delivered to the respiratory tract (e.g. nose or tracheas) and thus to the lung. In a preferred embodiment of the present invention, the UMSCs are delivered to the desired area by direct injection. The UMSCs as an active ingredient may also be formulated with a pharmaceutically acceptable vehicle to form a pharmaceutical composition in an appropriate form (e.g. as a cell suspension) for the purpose of delivery. Depending on the mode of administration, the pharmaceutical composition of the present invention preferably comprises about 0.1% by weight to about 100% by weight of the active ingredient, wherein the percentage by weight is calculated based on the weight of the whole composition. A "pharmaceutically acceptable vehicle" is non-toxic to a subject at the dosages and concentrations employed, and is compatible with the UMSCs and any other ingredients of any formulation comprising the UMSCs. For example, a suitable pharmaceutically acceptable vehicle for a formulation containing the UMSCs may include, but is not limited to, mannitol, water, Ringer's solution, and isotonic sodium chloride solution.

In some embodiments, solutions of UMSCs can be prepared in suitable isotonic liquids such as phosphate buffered saline, culture media, such as DMEM, physiological saline, aqueous dextrose, and/or mixtures thereof, and other suitable liquids known to those skilled in the art. The final therapeutic form should be protected against contamination and should be able to inhibit the growth of microorganisms such as bacteria or fungi. A single intravenous dose can be administered. Alternatively, a slow long term infusion or multiple short term daily infusions can be utilized. Alternate day or dosing once every several days can also be utilized, if needed.

The present invention is further illustrated by the following examples, which are provided for the purpose of demonstration rather than limitation. Those of skill in the art should, in light of the present disclosure, appreciate that many changes can be made in the specific embodiments which are disclosed and still obtain a like or similar result without departing from the spirit and scope of the invention.

Examples

Pulmonary fibrosis is a progressive and irreversible condition with various clinical causes, and no current medication or therapy can reverse the functionality of a fibrotic lung. This study investigated the feasibility of transplanting human umbilical mesenchymal stem cells (HUMSCs) into rats with pulmonary fibrosis and explored their underlying mechanisms. A stable left lung pulmonary fibrosis animal model was established by injecting 2 mg of bleomycin (BLM) into the trachea. On the twenty-first day after BLM injection, a low ($5 \times 10^6$) or high ($2.5 \times 10^7$) dose of HUMSCs was injected into the trachea.

Rats transplanted with low- or high-dose HUMSCs displayed significant reduction of fibrosis condition in the lung and recovery of the lung functionality at least in terms of blood oxygen saturation and respiratory rate as compared with the BLM rats.

1. MATERIALS AND METHODS 1.1 Experimental Animals

The use of human umbilical cords and laboratory animals in this study was approved by the Research Ethics Committee and Animal Research Committee of Kaohsiung Veterans General Hospital and National Yang-Ming University.

Six-week-old Sprague-Dawley (SD) rats weighing 200-250 g were obtained from the Laboratory Animal Center at NYMU. The rats were housed in transparent plastic cages ($45 \times 24 \times 20$ cm$^3$) under a 12:12 hour reversed light:dark cycle with light from 7:30 a.m. to 7:30 p.m. A constant temperature ($22 \pm 2°$ C.) was maintained, and food (Laboratory Animal Diets MF 18) and water were available ad libitum. Bedding was changed once weekly.

1.2 Establishing an Animal Model for Pulmonary Fibrosis in Left Lung

Various animal models have been developed for basic research into pulmonary fibrosis, including exposure to radiation (11), silica (12), asbestos (13), bacteria (14), and medications such as bleomycin (BLM) (15-19). Among the models, intra-tracheal BLM injection is most frequently applied because the time required for developing the disease is relatively short and the dosage required can be precisely controlled (18, 19). Because rats have only one lobe in the left lung and four in the right lung, each lobe of the lung may be affected differentially through intra-tracheal BLM injection each time the experiment is conducted. Therefore, the reproducibility of pulmonary fibrosis in each lobe of an animal model is inconsistent. Therefore, we injected BLM into the trachea and let the rat lay down by the left side 60° to develop a reproducible, severe, stable, and one-sided animal model of left lung pulmonary fibrosis. Thus, the therapeutic effect of transplanted stem cells could be precisely evaluated.

Male rats (SD rats; 200-250 g) were anesthetized through intraperitoneal injection using Zoletil 50 and xylazine hydrochloride (Sigma 23076359). The rats' neck fur was shaved off using clippers, and the skin was disinfected with povidone iodine-soaked cotton swabs and cut open. Subsequently, the muscles were separated until the trachea was revealed. Using a 30-G needle, 2 mg/200 μL BLM was injected into the trachea of the rat, which was then rotated to the left side by 60° for 90 minutes. The BLM was purchased from Nippon Kayaku Co., Ltd. The BLM stock solution (5 mg/100 μL) was obtained by dissolving BLM powder in sterile normal saline and storing at 4° C. When required, the stock solution was diluted 5-fold with normal saline to a working concentration of 1 mg/100 μL.

1.3 Isolation, Culture, and Transplantation of HUMSCs

Human umbilical cords were collected aseptically after delivery and kept at 4° C. in Hank's Balanced Salt Solution (HBSS). The HUMSCs were isolated within 24 hours after collection. All equipment was autoclaved before the experiments. During the experiment, all instruments were disinfected in 75% ethanol and flamed before reuse. In a laminar hood, the umbilical cords were disinfected in 75% ethanol and placed in the HBSS solution. Subsequently, the mesenchymal tissue (Wharton's jelly) was cut into small pieces and centrifuged at 4000 rpm for 5 minutes. After removing the supernatant fraction, the umbilical mesenchymal tissue was treated with collagenase and trypsin, followed by the addition of fetal bovine serum (FBS; Gibco 10437-028) to stop the reaction; at that point, the umbilical mesenchymal cells were fully processed into HUMSCs. Finally, the HUMSCs were suspended in 10% FBS Dulbecco's modified Eagle's medium (DMEM) for calculating cell number and for subsequent culturing.

The HUMSCs were treated with 0.05% Trypsin-EDTA (Gibco 15400-054) for 2.5 minutes. Cells were then collected, washed twice with 10%/o FBS DMEM, and centrifuged at 1500 rpm for 5 minutes; then, the supernatant was removed. The pelleted cells were subsequently suspended at the concentration of $5 \times 10^6$ or $2.5 \times 10^7$ in 200 μL of 0.1 M sterile phosphate-buffered saline (PBS).

Male rats (SD rats; 200-250 g) were anesthetized through intraperitoneal injection with Zoletil 50 and xylazine hydrochloride (Sigma 23076359). The rats' neck fur was shaved off with a clipper. The skin was asepticized with povidone iodine-soaked cotton swabs and cut, after which the muscles were separated until the trachea was revealed. Subsequently, $5 \times 10^6$ or $2.5 \times 10^7$ HUMSCs were transplanted into the tracheas of the rats by using a Hamilton needle.

1.4 Animal Groupings

The animals were divided into the following four groups:

| | Group | Treatment |
|---|---|---|
| 1 | Normal group: | 6-week-old rats that were intratracheally injected with 200 µL of saline. |
| 2. | BLM group: | 6-week-old rats that were intratracheally administered with 2 mg of BLM. These rats were sacrificed on Days 7, 14, 21, 28, and 49 |
| 3. | BLM + HUMSCs (LD) group: | 6-week-old rats that were intratracheally injected with 2 mg of BLM. On the twenty-first day after BLM injection, $5 \times 10^6$ HUMSCs were intratracheally transplanted. |
| 4. | BLM + HUMSCs (HD) group: | 6-week-old rats that were intratracheally injected with 2 mg of BLM. On the twenty-first day after BLM injection, $2.5 \times 10^7$ HUMSCs were intratracheally transplanted. |

Figure 1:
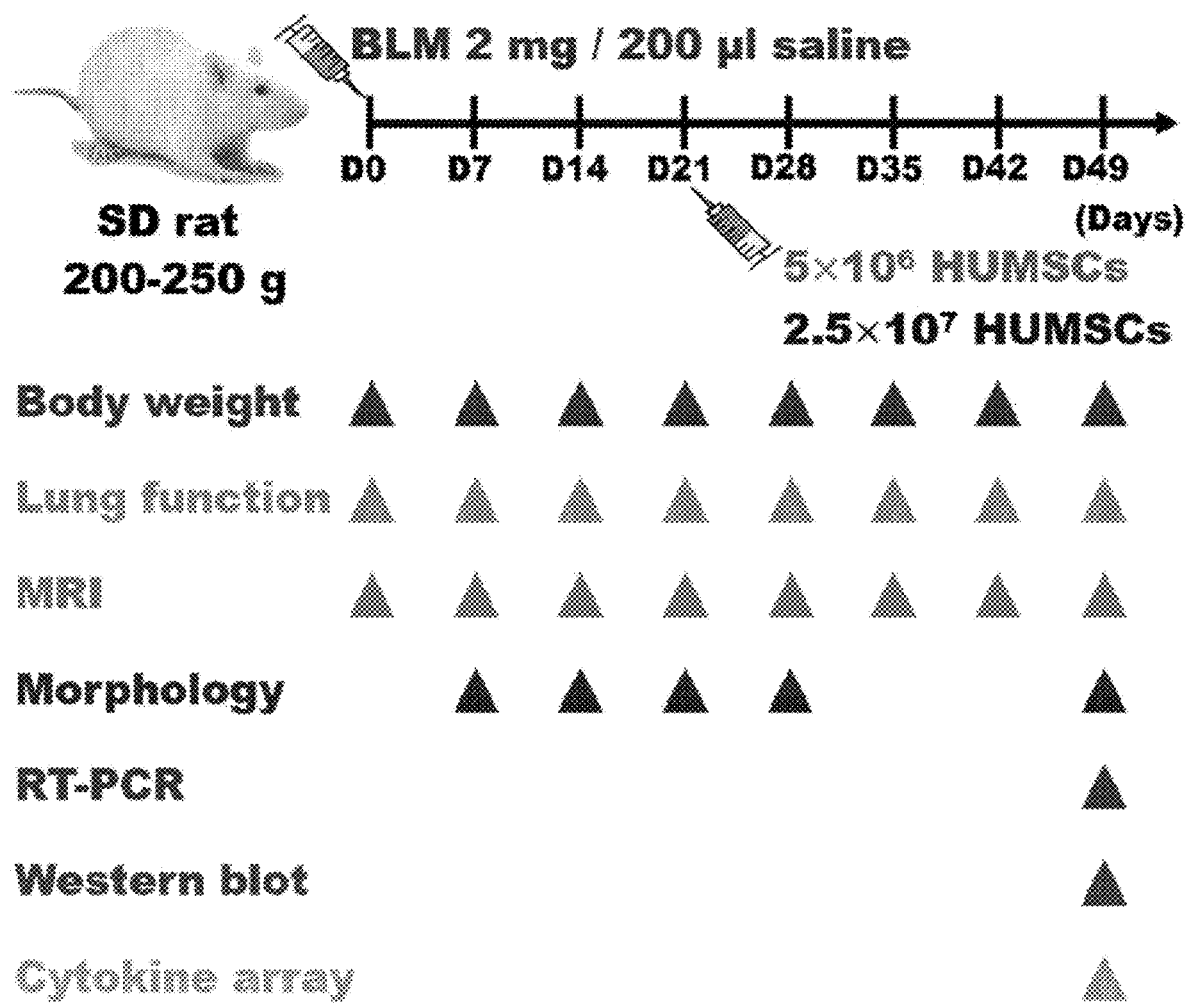
FIG. 1 shows experimental flowchart for inducing pulmonary fibrosis in rats' left lungs, the transplantation of HUMSCs, and the time course for various experiments in this study. Rats were sacrificed on various days after BLM treatment.

The experimental flowchart is displayed in FIG. 1.

1.5 Determination of Arterial Blood Oxygen Saturation

After shaving the fur on the rats' front legs, they were anesthetized with isoflurane (Baxter 228-194) for 40 minutes. The shaved legs were clipped with a pulse oximeter (Rossmax SB 100) for measuring arterial blood oxygen saturation.

1.6 Determination of Pulmonary Respiratory Rates

The experimental animals were placed in a closed cylinder-like detection chamber (whole body plethysmograph, emka Technologies), in which the alterations of breath flow were recorded for 15 minutes using the BIOPAC BSL 4.0 MP45 software package. The respiratory rates of the rats were also quantified when they were still.

1.7 Magnetic Resonance Imaging

Rat lung images were obtained through magnetic resonance imaging (MRI; BRUKER BIOSPEC 70/30) at the Instrumentation Center of National Taiwan University. The thoracic cavities of the rats were scanned from rostral to caudal and photographed horizontally every 1.5 mm until the whole thoracic cavity had been scanned. Because the first image obtained in each rat varies in position, the total number of images in the horizontal plane was 20 to 25.

Image-Pro Plus software was employed, and the carina of the trachea was used as a landmark for image positioning. Two slices before and after the carina as well as the slice including the carina (a total of five MRI images) were used to quantify the black alveolar spaces; thus, the left lung alveolar volume of the rat was obtained.

1.8 Sacrifice and Perfusion Fixation of Experimental Animals

The experimental animals of each group were anesthetized through intratracheal injection with Zoletil 50 and xylazine hydrochloride (Sigma 23076359) before perfusion. The animals were perfused with 0.1 M PBS, and then the left and right lungs were removed and immersed in a fixation solution with 4% paraformaldehyde (Sigma 10060) and 7.5% picric acid (Sigma 925-40) in 0.1 M PBS. Samples were postfixed at 4° C. for 3 days and then kept in a vacuum at room temperature for 6 hours. The left and right lungs were maintained in fixative solution at 4° C. for 2 days and then subjected to paraffin embedding and immunostaining.

1.9 Embedding Tissue into Paraffin Blocks and Sectioning

Following fixation, left and right lungs were passed through a series of increasing concentrations of alcohol (70%, 80%, 95%, and 95%) on a rocker for 20 minutes each. The samples were then submerged in 100% alcohol and dehydrated six times for 30 minutes each. After dehydration, tissues were immersed in xylene (J. T. Baker 9490-03) for approximately 1 minute, followed by 15 minutes in 1:1 xylene:paraffin and 15 minutes in 1:3 xylene:paraffin. Subsequently, tissues were submerged in pure paraffin three times for 30 minutes each. Finally the tissues were paraffin embedded.

Lung tissues were sectioned into 5-µm slices, which were flattened on the surface of warm water (40-45° C.), placed on microscope slides, and dried on a hot plate at 50° C.

A serial sagittal section was performed from the outermost lateral side. Ten slices were numbered consecutively and placed on slides for various immunohistochemistry (IHC) examinations. For example, in the Normal group, lung slices numbered from 1 to 10 were placed on slides lettered from A to J, and slices numbered from 11 to 30 were discarded (a total of 20). As the sectioning process was performed toward the hilum, slices numbered from 31 to 40 were placed on slides lettered from A to J, and another 20 slices were discarded. The procedure was repeated until the entire lung was completely sectioned. Thus, slices in column A (numbers: 1, 31, 61, 91, 121, . . . 871) were all subjected to hematoxylin and eosin (H&E) staining; lung slices in column B (numbers: 2, 32, 62, 92, 122, . . . 872) were stained with Sirius red for the evaluation of tissue fibrosis; lung slices in column C (numbers: 3, 33, 63, 93, 123, . . . 873) were subjected to IHC with anti-ED1 antibody to examine inflammatory responses; lung slices in column D (numbers: 4, 34, 64, 94, 124, . . . 874) were immunostained with anti-proSPC antibody for the labeling of AEC2s; lung slices in column E (numbers: 5, 35, 65, 95, 125, . . . 875) were subjected to immunostaining with anti-α-SMA antibody for the labeling of myofibroblasts; and lung slices in column F (numbers: 6, 36, 66, 96, 126, . . . 876) were subjected to immunostaining with anti-human specific nuclear antibody for labeling of HUMSCs. Rows A①-J①, A②-J②, and A③-J③ represent the outermost region of each lobe in a left lung and rows A⑥-J⑥ and A⑦-J⑦ represent the region close to a hilum of a left lung. The number of lung slices obtained varied between groups (330-880 slices). The remaining columns (G-J) were preserved as spares.

1.10 H&E Staining

Lung tissue sections were deparaffinized using xylene I and xylene II for 5 minutes each; rehydrated with 100%, 95%, 80%, and 70% ethanol followed by tap water for 5 minutes each; immersed in hematoxylin solution (Muto Pure Chemicals Co., Ltd; No. 3008-1) for 5 minutes; and washed in tap water for 30 minutes. Slides were then immersed in eosin solution (Muto Pure Chemicals Co., Ltd; No. 3200-2) for 2.5 minutes, dipped in acetic acid (glacial) for 3 seconds, rinsed in tap water, dehydrated through a series of increasing concentrations of alcohol (50%, 70%, 80%, 90%, 95%, 100%, and 100%) for 2 minutes each, and immersed in xylene twice for 5 minutes each. Finally, slides were mounted with permount and observed and photographed with an optical microscope.

1.11 Sirius Red Stain

After deparaffinization and rehydration, the lung tissue sections were immersed in 0.1% Sirius red (Sigma 2610-10-8) in Picric acid for 10 minutes, followed by immersion in ddH$_2$0 for 30 seconds. Subsequently, lung tissue sections were dehydrated through immersing in a series of increasing concentrations of alcohol (50%/c, 70%, 80% 90%, 95%, and 100% twice) for 30 seconds each, immersed in xylene twice for 5 minutes each, and finally mounted using a mounting medium. Slides were then observed and photographed using optical microscopy.

1.12 Immunohistochemistry

First, the dried lung$_{tissue}$ slices were deparaffinized, rehydrated, and placed in 0.296% trisodium citrate dihydrate (Kanto chemical 37150-00) solution, boiled for 10 minutes, and cooled to room temperature. Subsequently, the samples were immersed in 0.1 M PBS for 30 minutes, which allowed the antigens to recover for immunostaining.

The tissues slices (with recovered antigens) were washed three times with 0.1 M PBS for 5 minutes each, reacted with blocking solution (3% Bovine serum albumin, 1% Triton X-100, and 5% FBS) at room temperature for 60 minutes, reacted with primary antibodies (mouse anti-α-SMA antibody [Sigma; 1:400], mouse anti-ED1 antibody [Millipore; 1:400], or rabbit anti-proSPC [Millipore; 1:400]) at 4° C. for 12-18 hours, washed three times with 0.1 M PBS for 5 minutes each, and then reacted with secondary antibodies (goat anti-mouse-IgG-conjugated biotin [KPL; 1:250] or goat anti-rabbit-IgG-conjugated biotin [KPL; 1:250]) at room temperature for 60 minutes. Samples were then washed with 0.1 M PBS for 5 minutes each, reacted with avidin-biotinylated-horseradish peroxidase complex (ABC Kit, Vector Laboratories) at room temperature for 60 minutes, washed with 0.1 M PBS for 5 minutes each, and finally developed with 3,3'-diaminobenzidine (DAB; 5 mg of DAB and 3.5 μL of 30% $H_2O_2$ in 10 mL of Tris-HCl; pH 7.4).

After staining, the lung tissue slices were dried at room temperature, dehydrated by passing through a series of alcohols of increasing concentrations (50%, 70%, 80%, 90%, 95%, 100%, and 100%) for 30 seconds each, immersed in xylene twice for 5 minutes each, and finally mounted with mounting medium for observation and photographing under an optical microscope.

1.13 Tracing the Viability and Distribution of HUMSCs with Bisbenzimide

To trace the viability and distribution of the implanted HUMSCs, cells were labeled with 1 μg/mL bisbenzimide (Sigma B2883) for 48 hours before trypsinization with 0.05% Trypsin (Gibco 15400-054) and subsequent transplantation. Transplantation of HUMSCs was performed 21 days after BLM injection. After 1 month, the rats were sacrificed, perfused, and fixed, and associated protective procedures for cryosection were performed. The rats were perfused with 0.1 M PBS and fixed using 4% paraformaldehyde (Sigma 10060) and 7.5% picric acid (Sigma 925-40) in 0.1 M PB. Left and right lungs were obtained and immersed in fixative at room temperature for 6 hours in a vacuum and then at 4° C. for 16-18 hours. Subsequently, samples were placed in 30% sucrose in 0.1 M PBS at 4° C. until they sank to the bottom. Afterward, samples were embedded in tissue freezing medium and cryosectioned at 30 μm with a cryostat at −20° C. After mounting with Fluoromount Aqueous Mounting Medium (Sigma F4680-25 ml), the distribution of the HUMSCs was directly observed under a fluorescence microscope.

1.14 IHC Labeling of HUMSCs Using Anti-Human Nuclear Antigen

IHC was applied to observe the HUMSCs. Samples were reacted with mouse anti-human specific nuclei antigen (Millipore; 1:100) at 4° C. for 36-42 hours, washed with 0.1 M PBS three times for 5 minutes each, reacted with secondary antibody (goat anti-mouse-IgG-conjugated biotin [KPL; 1:250]) at room temperature for 60 minutes, and washed with 0.1 M PBS three times for 5 minutes each. Finally, the color was developed with DAB (5 mg of DAB and 3.5 μL of 30% $H_2O_2$ in 10 mL of Tris-HCl; pH 7.4) to trace the viability of the HUMSCs in the rat lungs.

1.15 Reverse Transcription Polymerase Chain Reaction (RT-PCR)

Total RNA of the lung tissue was extracted using TRIzol®Reagent (Invitrogen® 15596-018). After quantification, 2 μg of RNA was subjected to reverse transcription. After cDNA was synthesized, it was diluted 10-fold, and 1 μL of cDNA was used for polymerase chain reaction with the following primers:

(1) Human surfactant protein D (SP-D):

```
                                      (SEQ ID NO: 1)
F:         5'-AGGAGCAAAGGGAGAAAGTGG-3';

(SEQ ID NO: 2)
R:         5'-GCTGTGCCTCCGTAAATGGT-3'
```

(2) Human platelet endothelial cell adhesion molecule (PECAM-1):

```
                                      (SEQ ID NO: 3)
F:         5'-TCAAGAAAAGCAACACAGTCC-3';

(SEQ ID NO: 4)
R:         5'-ACTCCGATGATAACCACTGC-3'
```

(3) Human GAPDH

```
                                      (SEQ ID NO: 5)
F:         5'-TCCTCCACCTTTGACGCT-3';

(SEQ ID NO: 6)
R:         5'-TCTTCCTCTTGTGCTCTTGC-3'
```

(4) Rat GAPDH

```
                                      (SEQ ID NO: 7)
F:         5'-CTCTACCCACGGCAAGTTCAAC-3';

(SEQ ID NO: 8)
R:         5'-GGTGAAGACGCCAGTAGACTCCA-3'
```

(5) Human/Rat β-actin

```
                                      (SEQ ID NO: 9)
F:         5'-TTGTAACCAACTGGGACGATATGG-3';

(SEQ ID NO: 10)
R:         5'-GATCTTGATCTTCATGGTGCTAGG-3'
```

The temperature settings were as follows: enzyme activation for 10 minutes at 95° C.; denaturing for 30 seconds at 95° C.; annealing for 30 seconds at 56-60° C.; and extension for 1 minute at 72° C. After 35 cycles of PCR, samples were finished for 5 minutes at 72° C. The PCR products were analyzed using 2% agarose gel electrophoresis and visualized in an ultraviolet transilluminator.

1.16 Western Blotting

Lung tissues from each group were placed in mortars and liquid nitrogen was added. After the samples were ground, lysis buffer (Millipore 20-188) was added and reacted overnight at 4° C. until homogenized. Samples were then centrifuged at 13,000 rpm at 4° C. for 30 minutes. Supernatants were obtained and protein contents were quantified.

For the separation of proteins, 5% stacking gel and 10% running gel were prepared. Lung tissue samples were loaded separately into individual wells. An empty well was loaded with a standard molecular-weight marker (protein marker; Fermentas SM0671). Running buffer was added to an electrophoresis chamber. The stacking and the running gels were run at 50 V and 120 V, respectively. The sodium dodecyl sulfate polyacrylamide gel electrophoresis (SDS-PAGE) apparatus was removed after electrophoresis.

The BIO-RAD Trans-Blot Semi-Dry Electrophoretic Transfer Cell was applied for transfer. The polyvinylidene (PVDF) membrane, SDS-PAGE apparatus, and filter papers were placed in order from the anode to cathode and rinsed with working transfer buffer. The SDS-PAGE proteins were transferred onto PVDF paper at 15 V for 50 minutes.

The PVDF paper was washed three times for 5 minutes each with 0.1% PBST solution (0.1% Tween-20 in 0.1 M PBS), blocked with blocking solution (3% Albumin bovine serum in 0.1% PBST) at room temperature for 60 minutes, and reacted with primary antibodies (mouse anti-α-SMA antibody [Sigma; 1:1000], rabbit anti-proSPC antibody [Millipore; 1:1000], rabbit anti-matrix metallopeptidase 2 (MMP-2) antibody [Abcam; 1:1000], rabbit anti-matrix metallopeptidase 9 (MMP-9) antibody [Abcam; 1:1000], mouse anti-TLR-4 antibody [Abcam; 1:1000], and mouse anti-β-actin antibody [Sigma; 1:10000] for internal control) at 4° C. for 12-18 hours. Subsequently, the membrane was reacted with the corresponding secondary antibodies (goat anti-mouse IgG conjugated peroxidase [Abcam, 1:10000] and goat anti-rabbit IgG conjugated peroxidase [Abcam, 1:10000]) at room temperature for 1 hour and washed with 0.1% PBST solution three times for 5 minutes each. Finally, the membrane was removed, drained, and reacted with a chemiluminescent reagent (Bio-rad 170-5060). The signals were detected and photographed with a chemiluminescence detector (GE Healthcare, LAS4000-I biomolecular imager). The protein bands were quantified using ImageJ and normalized using individual internal controls for comparison.

1.17 Cytokine Array

A RayBio® Human Cytokine Antibody Array C2000 (RayBio® AAH-CYT-2000-8) was employed to detect the cytokines synthesized or secreted by HUMSCs. In addition, a RayBio® Rat Cytokine Antibody Array C2 (RayBio® AAR-CYT-2-8) was used to detect cytokines produced or secreted by the rat lung tissues. Protein samples from the lungs were prepared from the Normal, BLM, and BLM+ HUMSCs groups and maintained at −80° C. A sample with a concentration of 250 µg/mL was prepared in 1 mL of blocking buffer and reacted with the cytokine antibody array membranes at room temperature for 2 hours. The membranes were then washed with 2 mL of wash buffer three times for 5 minutes each, reacted with 1 mL biotinylated antibody cocktail at room temperature for 2 hours, and incubated with 2 mL diluted HRP-Streptavidin (1:1000) at room temperature for 2 hours. The membranes were then removed and reacted with chemiluminescent reagent (Bio-rad 170-5060). The signals were detected and photographed with a chemiluminescence detector (GE Healthcare, LAS4000-I biomolecular imager).

1.18 Statistical Analysis

All data were presented as mean±SEM (standard error of the mean). One- or two-way ANOVA was used to compare the means, and Fisher's least significant difference test was applied for multiple comparisons. A p value less than 0.05 was considered statistically significant.

Figure 2:
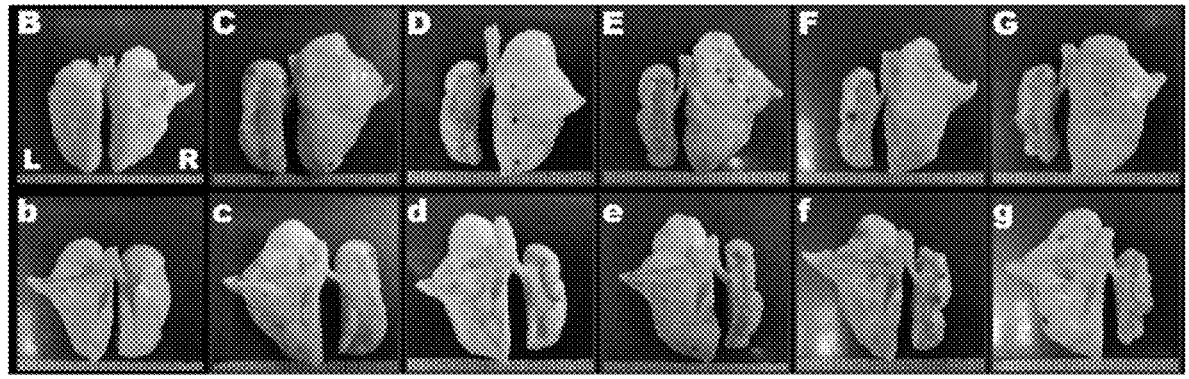
FIG. 2 shows the overall appearances of the anterior (B-I) or posterior (b-i) views of the left and right lungs of the rats in each group. The white alveolar structures are intact and smooth in both the left and right lungs of the Normal group (B and b). From Day 7 to 49 after BLM injection, the left lung markedly shrunk and healthy alveoli were only present at the perimeters of the left lungs; no alveoli appeared in the centers of the left lungs, except for pathologic tissues (C-G and c-g). Transplantation of high doses of HUMSCs significantly alleviated the shrinking of the left lungs in rats with pulmonary fibrosis (I and i).
Figure 2:
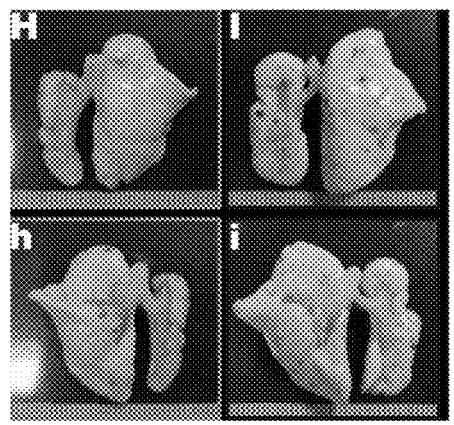

2. RESULTS 2.1 a One-Sided Left Lung Pulmonary Fibrosis Animal Model was Successfully Established in Rats Left and right lungs from each group were obtained and the morphology was examined. When observing the anterior and posterior views, a white alveolar structure was seen in the left and right lungs of the Normal group. The alveoli were intact and smooth (FIG. 2, panels B and b). On the seventh day after BLM injection, the left lungs had markedly shrunk and healthy alveoli were only present at their margins. No alveoli were present at the central region of the left lungs but pathologic tissues, scar tissues, were present (FIG. 2, panels C and c). On Days 14, 21, and 28 after BLM injection, the remaining alveoli had decreased slightly, and the pathologic tissue at the central region of the left lungs had shriveled and remained until Day 49 after drug administration (FIG. 2, panels D-G and d-g).

The left lungs were observed and photographed individually from the anterior and posterior views. The white left lung alveoli were intact in the Normal group. On the seventh day after BLM injection, healthy alveoli were only present in the outer peripheral region of the left lungs in the BLM rats. The alveoli disappeared in the central region of the left lungs and some connective tissue-like structures appeared. From 14 to 49 days after BLM injection, the connective tissues in the central areas became shriveled.

Figure 3A:
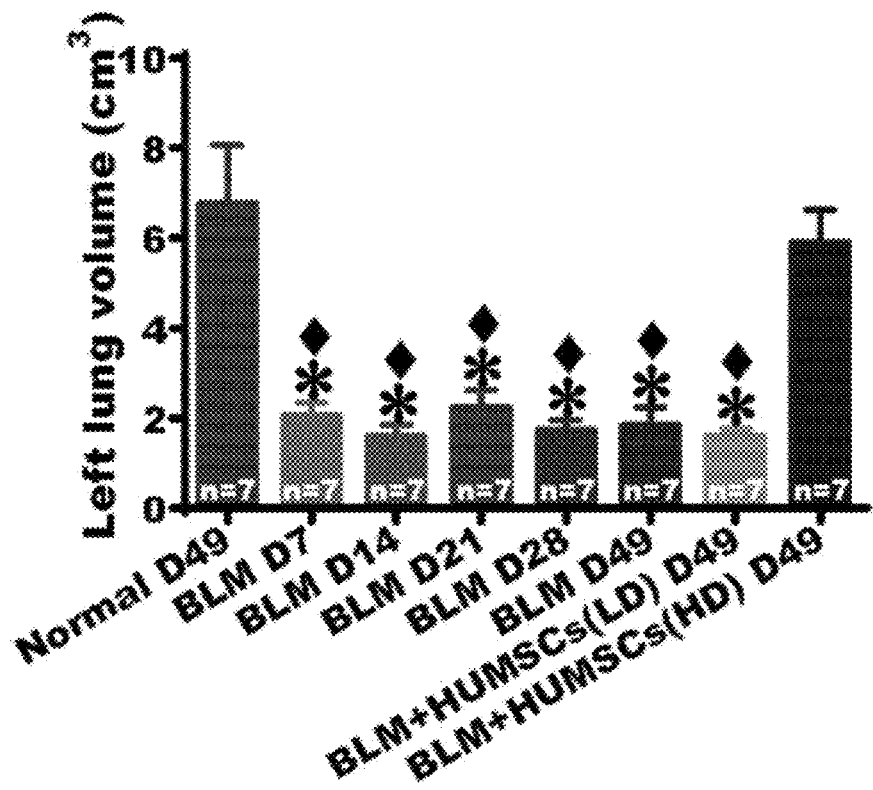
FIGS. 3A, 3B, 3C and 3D include charts showing the quantified results of the rats in each group, regarding left lung volume (FIG. 3A), left lung air space (FIG. 3B) and cell infiltration areas (FIG. 3C) by H&E staining, and collagen in the left lung (FIG. 3D) by Sirius red staining. The left lung tissue slices from each group were stained with H&E. The results revealed a massive cell infiltration in the center areas of the left lungs after BLM injection. Transplantation of high doses of HUMSCs ameliorated cell infiltration conditions in the central areas of the left lungs. The total left lung volume was quantified by summing data from all left lung sections, demonstrating that the transplantation of high doses of HUMSCs substantially increased the total left lung volume (FIG. 3A), raised left lung air space (FIG. 3B), and effectively reduced cell infiltration areas in the left lungs (FIG. 3C). Left lung sections were stained with Sirius red in each group. Massive stained regions appeared in the left lungs after Day 21 and were maintained until Day 49. The transplantation of HUMSCs reduced collagen in the left lung (FIG. 3D). ✱: $p<0.05$ versus the Normal group. #: $p<0.05$ versus the BLM group. ▲: $p<0.05$ versus the BLM+HUMSCs (LD) group. ♦: $p<0.05$ versus the BLM+HUMSCs (HD) group.
Figure 3B:
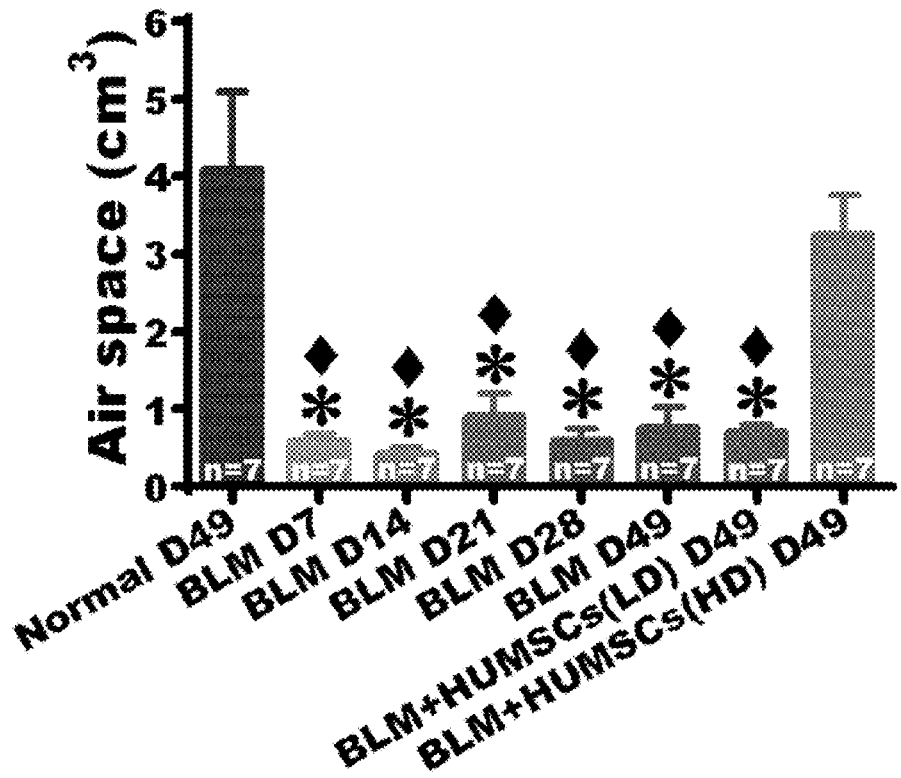
Figure 3C:
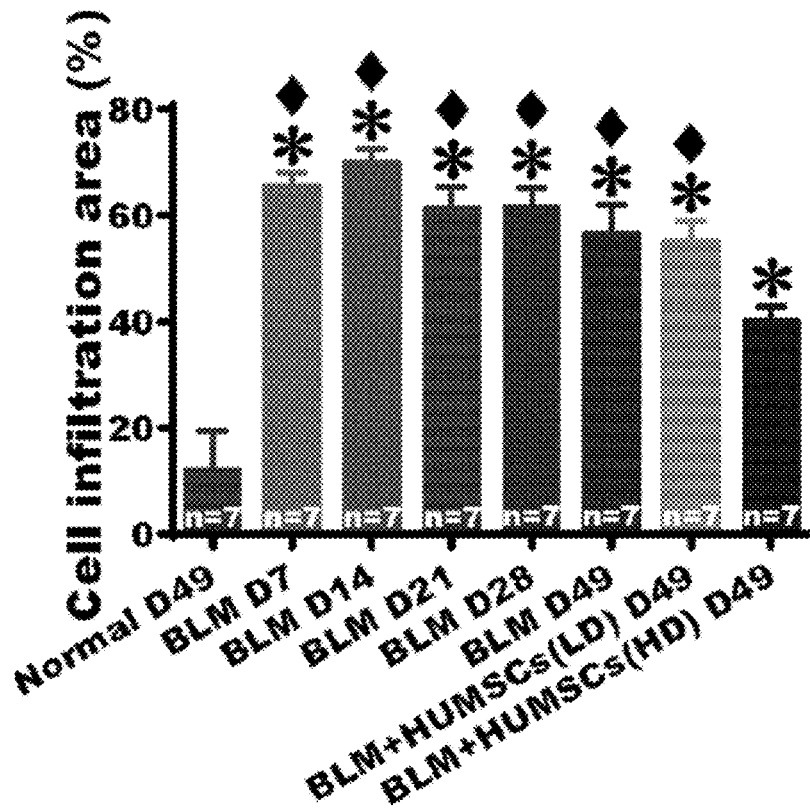

The left lung tissue slices from each group were stained with H&E. According to the results, the alveoli were shown to be intact, and the connective tissues were mostly present near the bronchus in the Normal group. In the BLM group, from 7 to 49 days after BLM injection, intact alveoli were only present in the peripheral regions of the left lungs. The central areas displayed substantial cell infiltration. After summing the results of the left lung sections stained with H&E, the left lungs were shown to have significantly shrunk to $2.08\pm0.67$ cm$^3$ in volume, beginning 7 days after BLM injection. Some alveolar structures ($0.59\pm0.22$ cm$^3$) still existed in the shrunk lungs, but consolidated tissues with substantial cell infiltrations occupied nearly 66% of the volume of the left lung. This situation remained until 49 days after BLM injury (FIG. 3A, FIG. 3B, FIG. 3C).

Figure 3D:
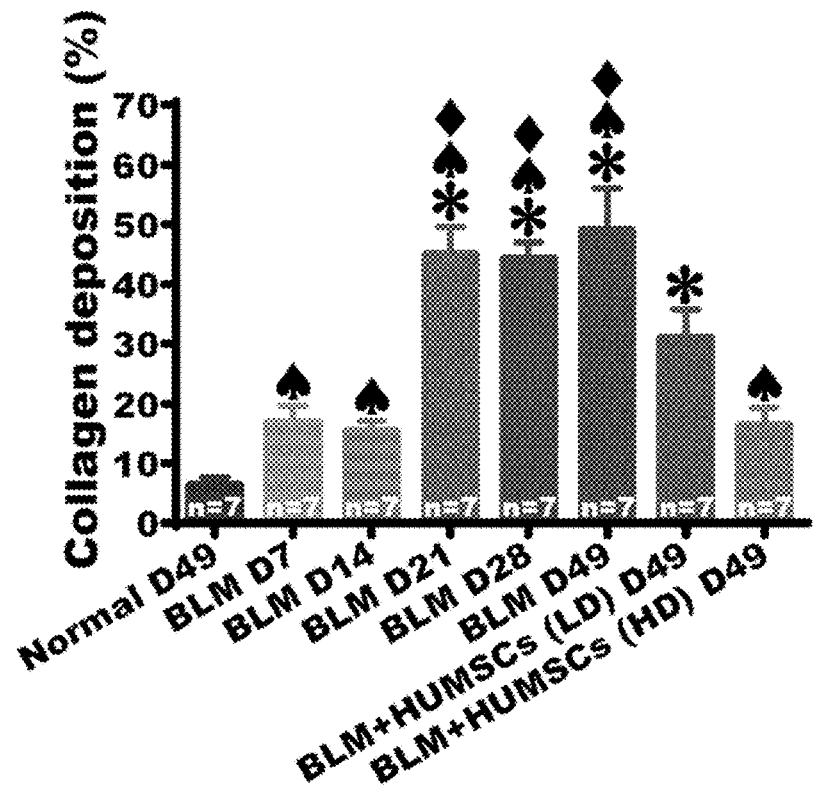

The tissue slices from the left lungs from each group were stained with Sirius red, and captured at low and high magnifications. Because the collagen was stained red, it appeared predominantly near the bronchus and blood vessels in the Normal group. In the left lungs of the BLM group, the areas with collagen exhibited no significant increase on Days 7 and 14 after BLM injection (FIG. 3D). From 21 days after BLM injection, the areas with collagen markedly increased, indicating advanced pulmonary fibrosis (FIG. 3D). This condition was sustained until Day 49 without recovery. The fibrosis areas also remained stable from Day 21 to 49 (FIG. 3D). Therefore, stem cells were transplanted into the tracheas of the rats 21 days after BLM injection.

The morphologies indicated that the one-sided left lung pulmonary fibrosis animal model was successfully established.

2.2 Overall Lung Appearance and H&E Staining Indicated that the Transplantation of HUMSCs Ameliorated Left Lung Shrinkage and Restored Alveolar Structures in Rats with Pulmonary Fibrosis The anterior and posterior appearances of the left and right lungs of the BLM+HUMSCs (LD) group showed no significant improvement (FIG. 2, panels H and h). However, the white alveolar area and the entire left lung volume of the BLM+HUMSCs (HD) group substantially increased compared with those of the BLM-treated group (FIG. 2, panels I and i).

When the left lung was isolated and observed from anterior and posterior views, the pathological alterations that occurred in the left lungs of the BLM+HUMSCs (LD) group were similar to those of the BLM group. Nevertheless, compared with the BLM group, the alveoli in the left lungs were significantly improved in the BLM+HUMSCs (HD) group.

From the results of H&E staining of the BLM+HUMSCs (LD) group, healthy alveoli also existed in the peripheries. Serious cell infiltration remained in the central areas. In the left lungs of the BLM+HUMSCs (HD) group, the infiltrated areas were significantly reduced and the alveolar volume was substantially increased in the central region. The total lung volume, air space, and cell infiltration area were similar between the BLM+HUMSCs (LD) and BLM groups. No statistical differences were identified. The lung volume remained at 5.90±1.76 cm$^3$, and the air space was approximately 3.26±1.23 cm$^3$ in the BLM+HUMSCs (HD) group. These values were comparable with the Normal group. Compared with the BLM group, the volume occupied by the connective tissue and infiltrated by cells significantly declined, suggesting that transplantation of high doses of HUMSCs reduces cell infiltration, increases total volume, and restores air space in the left lungs of rats with pulmonary fibrosis (FIG. 3A, FIG. 3B, FIG. 3C).

2.3 Sirius Red Staining Indicated that Transplantation of HUMSCs Reduced Collagen Deposits in Rats with Pulmonary Fibrosis In the left lungs of the BLM+HUMSCs (LD) group, the percentage of collagen deposited on Day 49 significantly decreased compared with that of the BLM-treated group on Days 21 to 49. However, this percentage remained significantly higher than that of the Normal group. The percentage of collagen deposition in the BLM+HUMSCs (HD) group was not only lower than that in the BLM group (Day 21 to 49) but also not significantly different to that of the Normal group (FIG. 3D). This suggests that the transplantation of HUMSCs reduces collagen deposition in rats with pulmonary fibrosis.

Figure 4A:
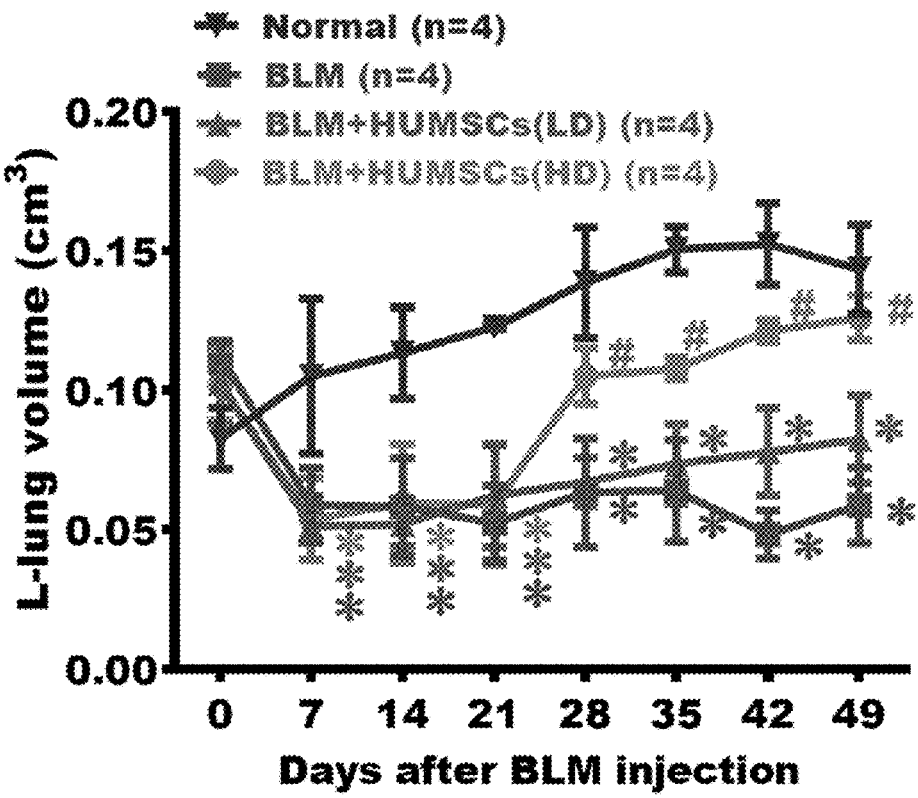
FIGS. 4A, 4B and 4C include charts showing the quantified results of the rats in each group, regarding left lung volume by MRI scans (FIG. 4A) and number of alveoli (FIG. 4B), and circumstance of alveoli (FIG. 4C) by H&E staining. MRI scans of rats' thoracic cavities were conducted in each group. Using carina of the trachea as a landmark for image positioning, summing the black alveolar spaces in five MRI images for each rat The space occupied by alveoli is clearly seen in both the left and right lungs in the Normal group. On Day 7, alveolar space was significantly reduced in the left lung and white consolidated tissues appeared. On Day 14, the alveolar volume in the left lungs was almost completely lost and had become occupied by consolidated tissue, which was sustained until Day 49. Transplantation of high doses of HUMSCs effectively increased alveolar volume. In addition, the left lung tissue slices from each group were stained with H&E. With a relatively small morphology, the number of alveoli per unit area was relatively high in the Normal group. Following BLM, the morphology of the alveoli became larger, and therefore, the number of alveoli per unit area decreased. In the group transplanted with HUMSCs, the alveoli were relatively small in morphology. The quantification of the alveoli (FIG. 4B) and the circumference of the alveoli (FIG. 4C) per unit area in the peripheral regions of the left lung indicated that transplantation of HUMSCs effectively increased the number of alveoli and circumference per unit area for gas exchange. ✱: $p<0.05$ versus the Normal group. #: $p<0.05$ versus the BLM group. ▲: $p<0.05$ versus the BLM+HUMSCs (LD) group. ♦: $p<0.05$ versus the BLM+HUMSCs (HD) group.

2.4 MRI Scans Revealed that Transplantation of HUMSCs Increased Alveolar Volume in Left Lungs of Rats with Pulmonary Fibrosis The carina of trachea was used as a landmark for image positioning. Images of the carina and of two slices before and after the carina were used for quantification of the black alveolar space, which represented the left lung alveolar volume of the rats. According to the results obtained from MRI scanning, in a thoracic cavity, the black signals observed represent the volume occupied by alveoli, whereas white signals represent consolidated tissues. Because alveoli existed in both the left and right lungs of the Normal rats, black signals were observed to be predominant in the Normal rats (FIG. 4A). On the seventh day after BLM injection, white signals appeared because of inflammatory responses and cell infiltration occurred in the left lungs. On Day 14, the alveolar volume in the left lungs was almost completely lost and was occupied by consolidated tissue; this condition remained until Day 49 (FIG. 4A). In the BLM+HUMSCs (LD) and BLM+HUMSCs (HD) groups between Days 7 and 21, white signals appeared, and the alveolar volume disappeared and was occupied by consolidated tissue. HUMSCs were transplanted on Day 21 in the BLM+HUMSCs (LD) group; however, white consolidated tissues remained in the left lungs between Days 28 and 49. The alveolar volume did not differ significantly from that of the BLM group (FIG. 4A). In the left lungs of the BLM+HUMSCs (HD) group, the volume exhibited a significant increase compared with that of the BLM group. Moreover, no significant difference was observed between the BLM+HUMSCs (HD) and the Normal groups (FIG. 4A). Therefore, transplantation of HUMSCs increases left lung alveolar volume in rats with pulmonary fibrosis.

Figure 4B:
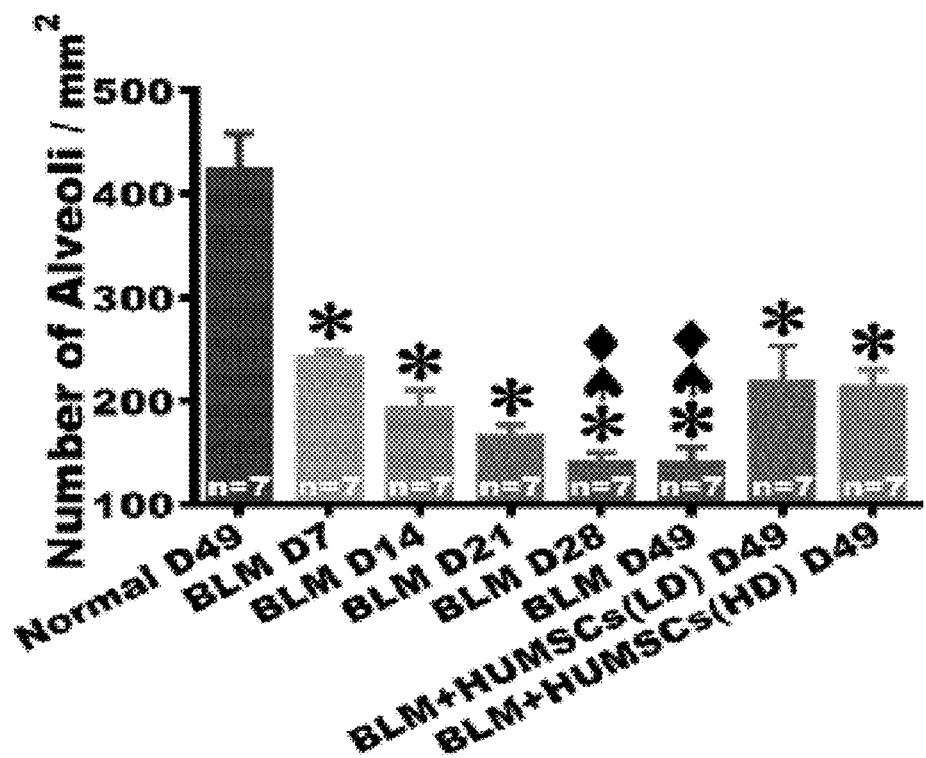
Figure 4C:
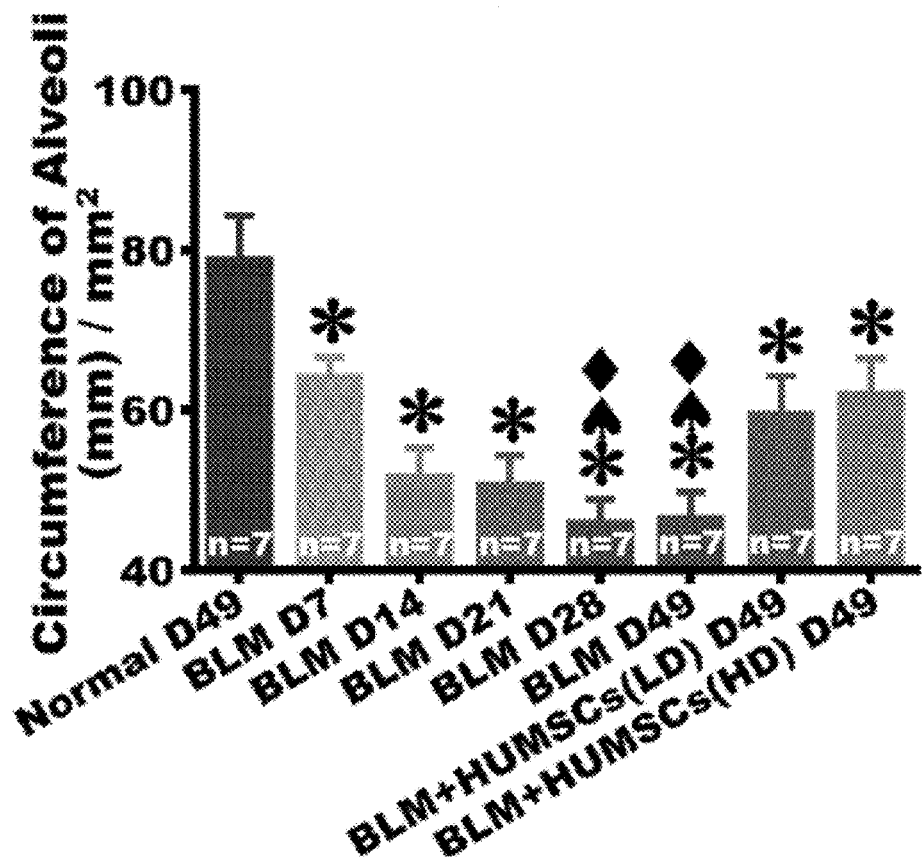

2.5 HE Staining Showed that the Transplantation of HUMSCs Improved Alveolar Gas Exchange in Rats with Pulmonary Fibrosis The tissue slices from the left lungs from each group were stained with H&E staining, and captured at low and high magnifications. In order to evaluated the efficacy of gas exchange in the peripheral regions of the left lungs, which alveolar structures still existed. Thus, the number and circumference of alveoli per unit of area at the peripheral regions of the left lungs were quantified to assess the efficiency of gas exchange. According to the results, in the Normal group, the H&E staining images reveal that the alveoli in the peripheries were smaller in size. Therefore, the number of alveoli per unit area was higher, and the total alveolar circumference for gas exchange was longer (FIG. 4B, FIG. 4C). From Day 7 to 49, the alveolar volume increased, which decreased the total number of alveoli per unit area. Furthermore, the alveolar circumference per unit area was significantly lower than that of the Normal group, suggesting that the effective area for gas exchange was reduced (FIG. 4B, FIG. 4C). In the BLM+HUMSCs (LD) and BLM+HUMSCs (HD) groups, the alveolar circumference and number of alveoli per unit area for exchanging gas had recovered significantly by Day 49 (FIG. 4B, FIG. 4C). This indicated that transplantation of HUMSCs improves the structure of the alveoli remaining in the peripheral regions of the left lungs of rats with pulmonary fibrosis, which in turn elevates gas exchange efficiency.

Figure 5:
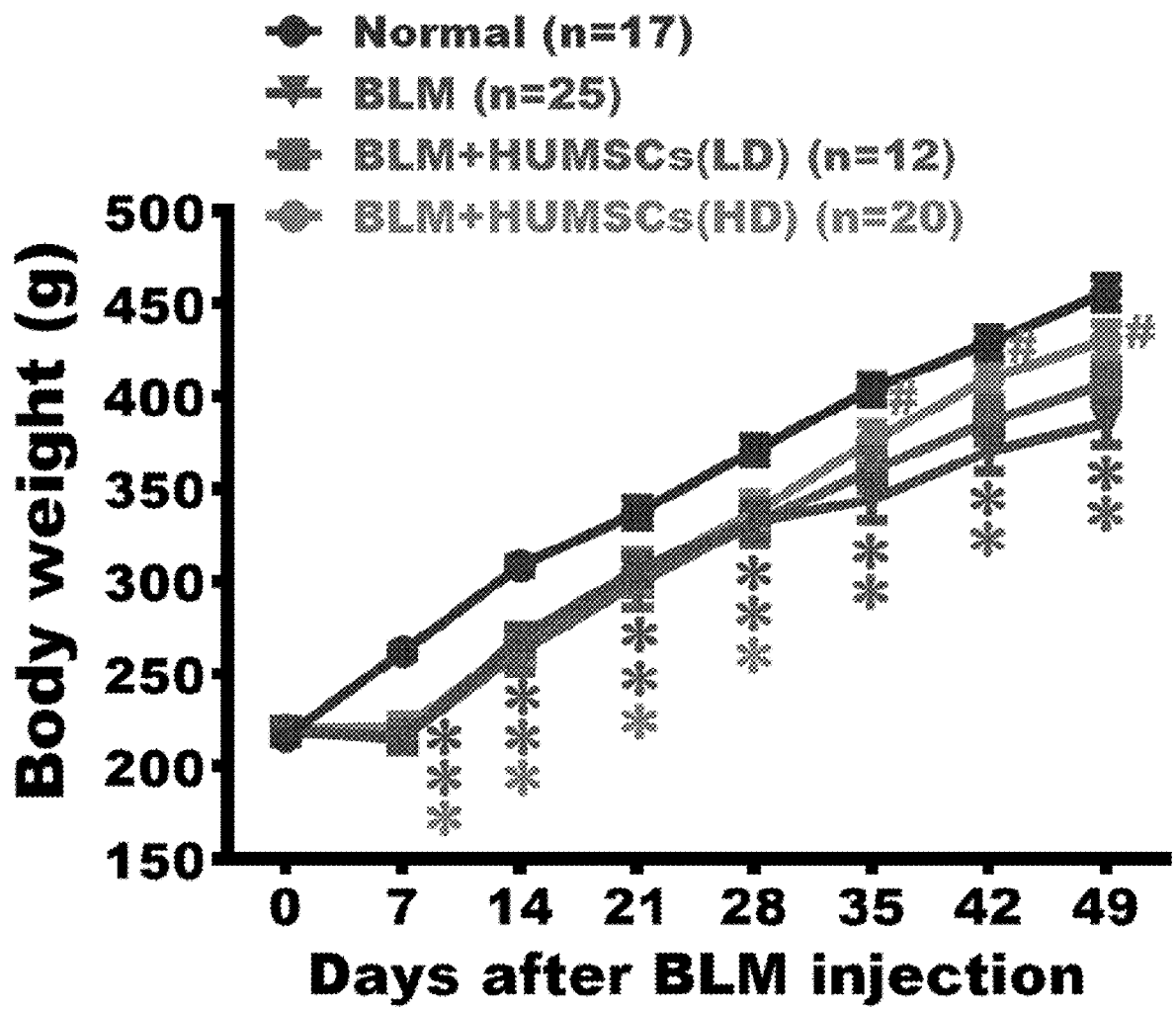
FIG. 5 shows the body weight of the rats in each group. The body weights of the rats in each group were documented for 7 weeks following Day 0, when the BLM had not yet been administered. The results indicated that the transplantation of high doses of HUMSCs improved the body weight of rats with pulmonary fibrosis. ✱: $p<0.05$ versus the Normal group. #: $p<0.05$ versus the BLM group.

2.6 Transplantation of HUMSCs Increased the Body Weight of Rats with Pulmonary Fibrosis Although the body weight of the Normal group increased over time, the weight of the BLM-treated group remained stagnant at Day 7. The body weights of the BLM rats increased over time, but they were significantly lower than those of the Normal group. In addition, this trend was sustained until 49 days after drug administration. In the BLM+HUMSCs (LD) and BLM+HUMSCs (HD) groups, the trends in body weight were similar to that of the BLM group; the weights were stagnant and lower than those of the Normal group on Day 7. From 7 to 49 days after BLM treatment, the weights of the rats in the BLM+HUMSCs (LD) group increased without a significant difference with the BLM group and were lower than those of the Normal group. However, on Day 35, the BLM+HUMSCs (HD) group showed a marked increases in weight compared with the BLM group, and the weights did not differ significantly from those of the Normal group, suggesting that transplantation of high doses of HUMSCs improved the weights of rats with pulmonary fibrosis (FIG. 5).

Figure 6A:
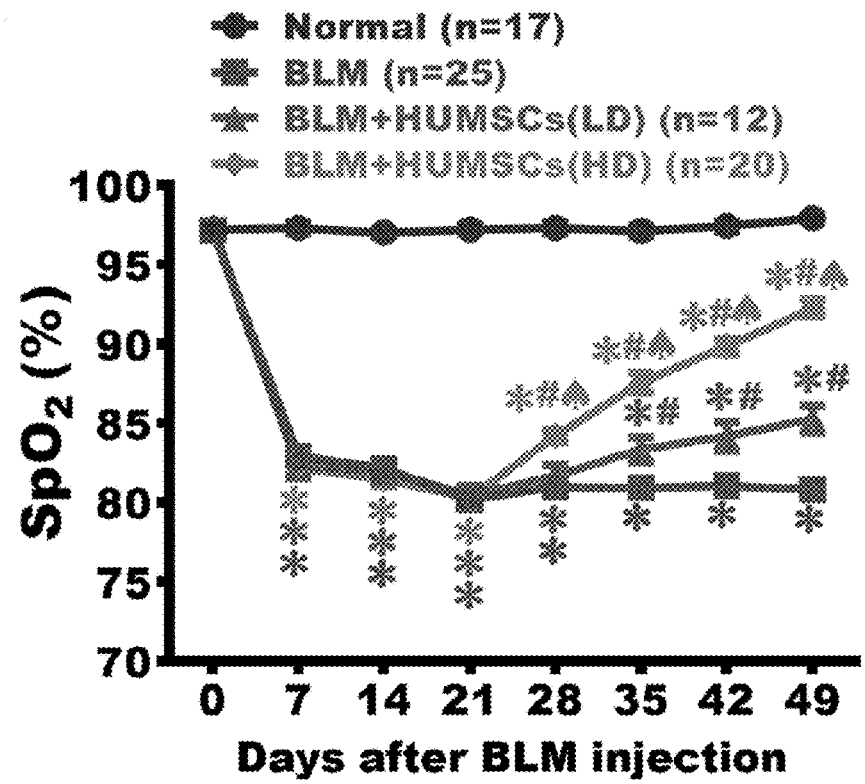
FIGS. 6A and 6B include charts showing HUMSCs alleviating pulmonary function in rats with pulmonary fibrosis. The rats in each group were examined for arterial blood oxygen saturation in their forelimbs. The results show that the $SpO_2$ on Day 49 was 98% in the Normal group, 80% in the BLM group, 85% in the BLM+HUMSCs (LD) group, and 93% in the BLM+HUMSCs (HD) group; demonstrating that the $SpO_2$ significantly was decreased on Day 7 and that this was sustained until Day 49 after BLM injection, and transplantation of HUMSCs helped to increase $SpO_2$ (FIG. 6A). Respiratory rates were recorded weekly for each group. In the Normal group, respiratory frequency was captured within 10 seconds or 2 seconds from Day 0 to 49. The quantitative results revealed that the respiratory frequency had significantly increased on Day 7, whereas the transplantation of stem cells helped to mitigate respiratory rate (FIG. 6B). ✱: $p<0.05$ versus the Normal group. #: $p<0.05$ versus the BLM group. ▲: $p<0.05$ versus the BLM+HUMSCs (LD) group.

2.7 Transplantation of HUMSCs Improved Arterial Oxygen Saturation in Rats with Pulmonary Fibrosis A pulse oximeter was used to analyze $SpO_2$ for evaluating the function of gas exchange. The results on Day 49 indicated that the arterial oxygen saturation ($SpO_2$) remained at 97.2%±0.8% in the Normal group (FIG. 6A). The $SpO_2$ of the BLM-treated group declined to 82.9%±3.2% on Day 7 and was maintained at 80%±2.7% until Day 49, which was significantly lower than that in the Normal group (FIG. 6A).

The $SpO_2$ markedly decreased from Day 7 to 21 in the BLM+HUMSCs (LD) and BLM+HUMSCs (HD) groups, exhibiting a similar trend to the BLM group. Because stem cells were transplanted on Day 21, an elevation in $SpO_2$ was observed in the BLM+HUMSCs (LD) group on Day 35. The $SpO_2$ increased continuously until Day 49, when the value reached 85.3%±3.0%, which was higher than that of the BLM group. However, compared with the Normal group, the SpO$_2$ of the BLM+HUMSCs (LD) group was significantly lower than that of the Normal group (FIG. 6A). For the BLM+HUMSCs (HD) group, a significant increase in SpO$_2$ was observed on Day 28, and the trend was maintained until Day 49 (SpO$_2$=92.3%+2.3%). Although the SpO$_2$ of the BLM+HUMSCs (HD) group exhibited a considerable improvement compared with the BLM and BLM+HUMSCs (LD) groups, it was significantly lower than that of the Normal group (FIG. 6A). These results indicate that the transplantation of HUMSCs improves gas exchange in rats with pulmonary fibrosis.

Figure 6B:
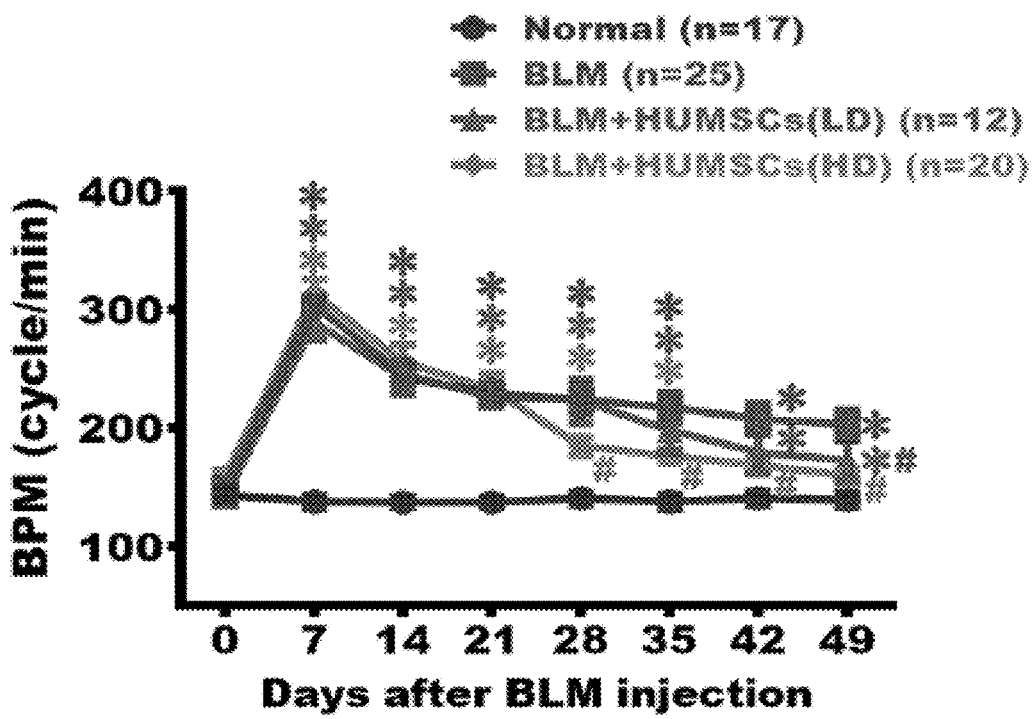

2.8 Transplantation of HUMSCs Mitigated the Symptoms of Rapid Respiratory Rate in Rats with Pulmonary Fibrosis Breaths per minute (BPM) were counted and captured within 10 seconds and 2 seconds to estimate lung function. From the qualitative figures obtained, the respiratory rates were shown to remain stable in the Normal group with 4 to 5 breaths every 2 seconds From Day 7 to 49 (FIGS. 3G and K). The respiratory rates had significantly increased to 303.90±48.77 and 203.37±54.34 BPM on Days 7 and 49 after BLM injury, respectively (FIG. 6B). In the BLM+HUMSCs (LD) and BLM+HUMSCs (HD) groups, the respiratory rates had significantly increased from Day 7 to 21, a trend similar to that of the BLM-treated group. In the BLM+HUMSCs (LD) group on Day 49, the respiratory rates had decreased to 172.19±58.28 BPM (FIGS. 3I and K). For the BLM+HUMSCs (HD) group, the respiratory rate had recovered on Day 28 compared with that of the BLM group, and this improvement was sustained until Day 49 (FIG. 6B). Thus, the transplantation of HUMSCs enhances respiratory function in rats with pulmonary fibrosis and thereby mitigates the symptoms of rapid respiratory rate.

Figure 7:
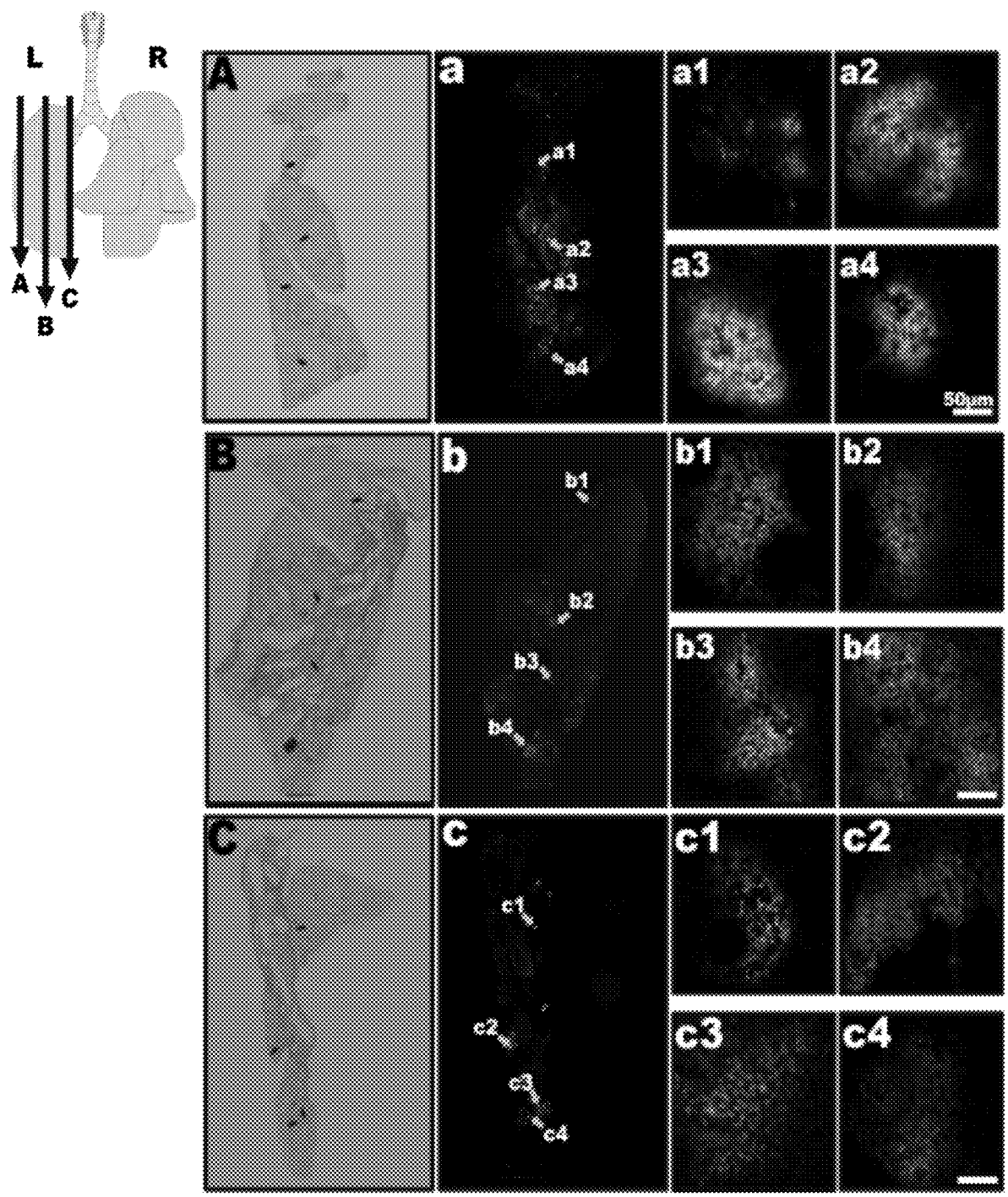
FIG. 7 shows that HUMSCs survived and were scattered in the left lungs of rats with pulmonary fibrosis by fluorescence assays. HUMSCs cultured in vitro were treated with bisbenzimide for 48 hours for nucleus labeling. They were subsequently transplanted into the trachea of rats 21 days after BLM injection. At 4 weeks after transplantation, serial cryosectioning was performed. A substantial number of live HUMSCs were found scattered in the lateral (A, a, a1-a4), intermediate (B, b, b1-b4), and inner parts (close to the hilum; C, c, c1-c4) of the lungs in the BLM+HUMSCs (HD) group. The upper-left image represents the locations of the slices. Panels A, B, and C are phrase images corresponding to different locations in the left lungs; a, b, and c are fluorescence images of A, B, and C, respectively; and a1-a4, b1-b4, and c1-c4 are magnified images of different regions of a, b, and c, respectively.

2.9 Transplanted HUMSCs Survived and were Scattered in the Left Lung of Rats with Pulmonary Fibrosis Cultured HUMSCs were treated with bisbenzimide, the nuclei of the HUMSCs were labeled in blue fluorescence, and the HUMSCs were transplanted into the trachea of rats on Day 21. After 4 weeks, the lungs were serially cryosectioned. A substantial number of live HUMSCs labeled with blue fluorescence were observed scattered over the lateral (FIG. 7, panels A, a, a1-a4), central (FIG. 7, panels B, b, b1-b4), and inner parts (close to the hilum; FIG. 7, panels C, c, c1-c4) of the left lung in the BLM-treated rats. The results reveal that the HUMSCs labeled with bisbenzimide survived and were distributed throughout the left lungs of the rats.

Figure 8:
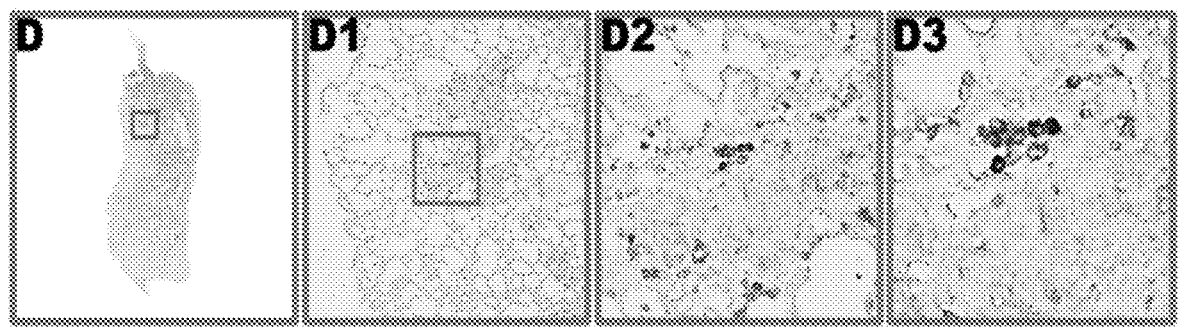
FIG. 8 shows the results of IHC performed with anti-human nuclei antibody for labeling of HUMSCs. From low to high magnifications, numerous HUMSCs were observed to be scattered in the left lungs of both the low dose (panels D, D1-D3) and high dose groups (panels E, E1-E3).
Figure 8:
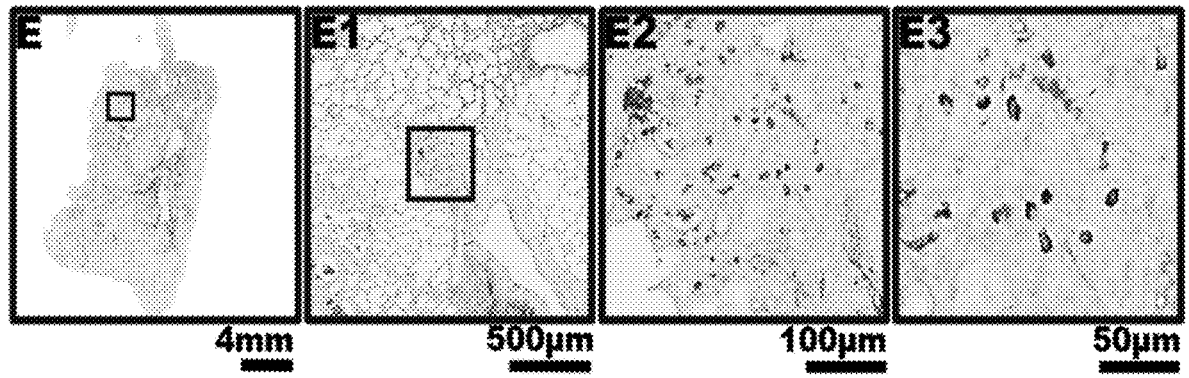

Moreover, anti-human specific nuclei antigen antibody was used in IHC to label HUMSCs. In the left lungs of both the BLM+HUMSCs (LD) and BLM+HUMSCs (HD) groups, HUMSCs were found in the connective tissues and distributed among the alveoli (FIG. 8, panels D, D1-D3, E, and E1-E3).

Figure 9:
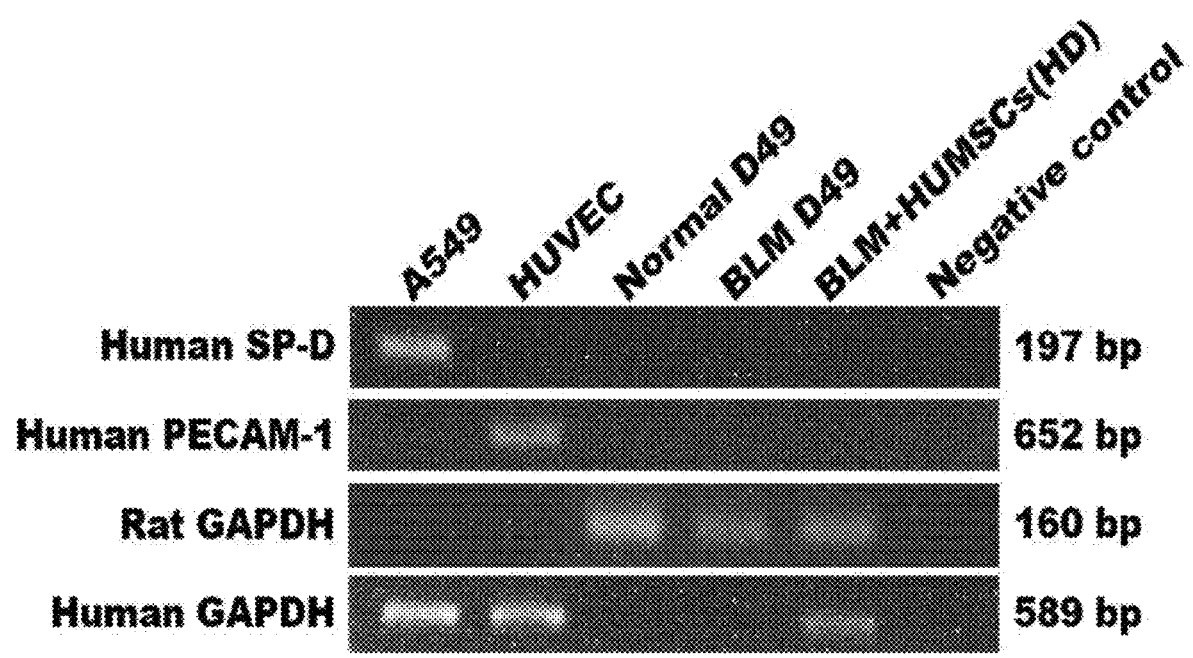
FIG. 9 shows the differentiation status of HUMSCs in the rats' left lungs. The differentiation of HUMSCs was examined using RT-PCR. A549 is a human adenocarcinoma cell line and was used as a positive control for human SP-D and human GAPDH. Human umbilical vein endothelial cells were applied as positive controls for human PECAM-1 and human GAPDH. The results indicated that HUMSCs located in the rats' left lungs do not differentiate into alveolar epithelial or vascular endothelial cells.

2.10 HUMSCs Transplanted into Rat Lungs Did not Differentiate into Alveolar Epithelial Cells and Vascular Endothelial Cells On Day 49, the left lung tissues of the Normal, BLM-treated, and BLM+HUMSCs (HD) groups were subjected to RNA extraction. After converting to cDNA, primers of human surfactant protein D (SP-D) and human platelet endothelial cell adhesion molecule (PECAM-1) were used to examine whether HUMSCs had differentiated into human alveolar or vascular endothelial cells. Because the BLM+HUMSCs (HD) group received a transplantation of HUMSCs, which remained in the left lung tissues 4 weeks after transplantation, RT-PCR detected an expression of human GAPDH. However, expressions of human SP-D or PECAM-1 were not detected, indicating that the HUMSCs did not differentiate into alveolar or vascular endothelial cells. This suggests that repair to the rats' fibrotic lungs was not achieved through the differentiation of transplanted HUMSCs (FIG. 9).

Figure 10:
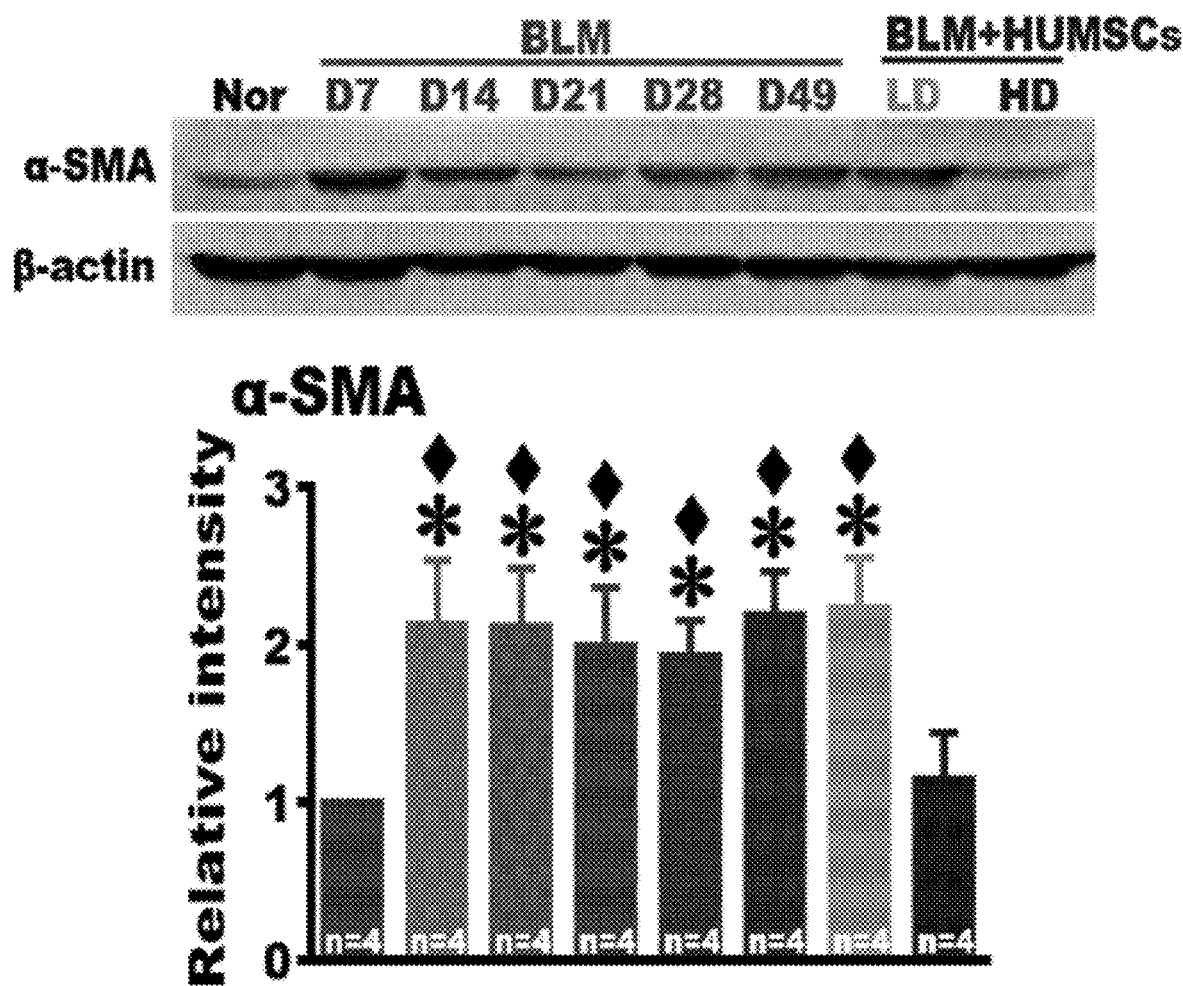
FIG. 10 shows that HUMSCs reduced the activation of fibroblasts in the left lungs of rats with pulmonary fibrosis.

2.11 Transplantation of HUMSCs Decreased the Activation of Fibroblasts in the Left Lungs of Rats with Pulmonary Fibrosis Anti-α-SMA antibody was used for IHC and Western blotting to detect and quantify activated fibroblasts. Few activated fibroblasts were discovered in the left lungs of the Normal group. The expressions of α-SMA in the BLM group were significantly higher than in those of the Normal group from Day 7 to 49 (FIG. 10). On Day 49, the expression of α-SMA in the BLM+HUMSCs (LD) group was not significantly recovered compared with the BLM group. In the BLM+HUMSCs (HD) group, the expression of α-SMA was markedly reduced on Day 49, suggesting that the transplantation of high doses of HUMSCs reduces the activation of fibroblasts in the left lungs of rats with pulmonary fibrosis (FIG. 10).

2.12 Transplantation of HUMSCs Triggered the Activation of Macrophages and Facilitated the Degradation of Collagen by Increasing the Synthesis of MMP-9 in the Left Lungs of Rats with Pulmonary Fibrosis Left lung sections were subjected to IHC with anti-ED1 antibody to label the macrophages. According to the results of immunohistochemistry, few macrophages, with a relatively small size, were found in the Normal group. On Days 7 and 14, the macrophages residing in the left lung were extensively activated, with an increased number and a larger size in terms of morphology. However, from Day 21 to 49, the number of activated macrophages decreased. In the BLM+HUMSCs (LD) and BLM+HUMSCs (HD) groups, the activated macrophages that were scattered in the connective tissues and alveoli were relatively large.

In addition, protein expressions of MMP-9 and MMP-2 in the left lungs were quantified through Western blotting. The transplantation of either low doses or high doses of HUMSCs was found to increase MMP-9, whereas no significant difference was observed for MMP-2. Thus, the increase of MMP-9 may facilitate the degradation of collagen in fibrotic regions (FIG. 11).

To further explore whether increases in MMP-9 were due to HUMSCs or macrophages, double-fluorescence staining was conducted with either anti-MMP-9 and anti-ED1 or anti-MMP-9 and anti-human nuclei. According to the staining results, numerous cells were stained with MMP-9 in the BLM+HUMSCs (HD) group, most of which were synthesized by macrophages. However, colocalization of MMP-9 and HUMSCs was barely observed. Furthermore, when anti-ED1 and anti-human nuclei antibodies were used for double-fluorescence staining, ED1-positive macrophages and HUMSCs were barely colocalized. This suggests that transplantation of HUMSCs stimulates the activation of autologous macrophages, which extensively synthesize MMP-9 and thereby assist with the degradation of collagen.

2.13 Transplantation of HUMSCs Enhanced TLR-4 Expression and Facilitated Recovery of Alveolar Epithelial Cells in the Left Lungs of Rats with Pulmonary Fibrosis Toll-like receptor 4 (TLR-4) is known as an indicator of restoration of alveolar epithelial cells (26), TLR-4 was quantified through Western blotting; only a small amount was expressed in the left lungs of both the Normal and BLM groups. By contrast, the expression of TLR-4 was significantly increased in the BLM+HUMSCs (LD) and BLM+HUMSCs (HD) groups, indicating that transplantation of HUMSCs enhances the synthesis of TLR-4 in the left lungs of rats with pulmonary fibrosis, indicating the promotion of restoration of alveolar epithelial cells (FIG. 12).

2.14 Transplanted HUMSCs Released Cytokines that Facilitated the Recovery of Lungs in Rats with Pulmonary Fibrosis To investigate whether HUMSCs transplanted into rat lungs secrete human cytokines and whether they alter rats' autologous cytokine profile, Human Cytokine Antibody Array and Rat Cytokine Antibody Array were used to examine the alterations of 174 human cytokines and 34 rat cytokines, respectively. Substantial amounts of human FGF-6 and IGF-1 existed in the left lungs of rats in the BLM+HUMSCs (HD) group (FIG. 13A). Furthermore, the injuries caused by BLM resulted in substantial increases in autologous IL-13, leptin, LIX, L-selectin, and MCP-1 (FIG. 13B). The transplantation of high doses of HUMSCs also stimulated the increased production of β-NGF, fractalkine, and GM-CSF (FIG. 13B).

3. CONCLUSIONS

In this study, HUMSCs were xenografted into the lungs of rats with pulmonary fibrosis. The transplanted HUMSCs did not differentiate into somatic cells but secreted a variety of cytokines that effectively reversed pulmonary fibrosis. Three underlying therapeutic mechanisms exist. First, HUMSCs inhibited an inflammatory response, reduced myofibroblast activity, and prevented the synthesis of more collagen. Second, HUMSCs activated the host's macrophages, which synthesized a substantial amount of MMP-9, which degraded the collagen present. Third, HUMSCs promoted restoration of alveolar epithelial cells that is required for regeneration of lung tissues. We therefore provide a new and effective therapeutic strategy for patients with pulmonary fibrosis using HUMSCs, which not only prevents progression of inflammatory responses and formation of fibrosis but also promotes degradation of fibrotic tissues that have occurred and restoration of alveolar epithelial cells for regeneration in the lung and thus fundamentally make the patients recover from the fibrotic damages.

REFERENCES

1. Barkauskas C E, Cronce M J, Rackley C R, Bowie E J, Keene D R, Stripp B R, Randell S H, Noble P W, and Hogan B L. Type 2 alveolar cells are stem cells in adult lung. *The Journal of clinical investigation.* 2013; 123(7): 3025-36.
2. Hogan B L, Barkauskas C E, Chapman H A, Epstein J A, Jain R, Hsia C C, Niklason L, Calle E, Le A, Randell S H, et al. Repair and regeneration of the respiratory system: complexity, plasticity, and mechanisms of lung stem cell function. *Cell stem cell.* 2014; 15(2):123-38.
3. Desai T J, Brownfield D G, and Krasnow M A. Alveolar progenitor and stem cells in lung development, renewal and cancer. *Nature.* 2014; 507(7491):190-4.
4. Tomasek J J, Gabbiani G, Hinz B, Chaponnier C, and Brown R A. Myofibroblasts and mechano-regulation of connective tissue remodelling. *Nature reviews Molecular cell biology.* 2002; 3(5):349-63.
5. Bois RMd. Strategies for treating idiopathic pulmonary fibrosis. *Nature reviews Drug discovery.* 2010; 9(2):129-40.
6. Wynn T A. Integrating mechanisms of pulmonary fibrosis. *The Journal of experimental medicine.* 2011; 208(7): 1339-50.
7. Wolters P J, Collard H R, and Jones K D. Pathogenesis of idiopathic pulmonary fibrosis. *Annual review of pathology.* 2014; 9(157-79.
8. Noble P W, Barkauskas C E, and Jiang D. Pulmonary fibrosis: patterns and perpetrators. *The Journal of clinical investigation.* 2012; 122(8):2756-62.
9. Li M, Krishnaveni M S, Li C, Zhou B, Xing Y, Banfalvi A, Li A, Lombardi V, Akbari O, Borok Z, et al. Epithelium-specific deletion of TGF-beta receptor type II protects mice from bleomycin-induced pulmonary fibrosis. *The Journal of clinical investigation.* 2011; 121(1):277-87.
10. Moseley P L, Hemken C, and Hunninghake G W. Augmentation of Fibroblast Proliferation by Bleomycin. *The Journal of clinical investigation.* 1986; 78(1150-4.
11. Jackson I L, Xu P, Hadley C, Katz B P, McGurk R, Down J D, and Vujaskovic Z. A preclinical rodent model of radiation-induced lung injury for medical countermeasure screening in accordance with the FDA animal rule. *Health physics.* 2012; 103(4):463-73.
12. Barbarin V, Nihoul A, Misson P, Arras M, Delos M, Leclercq I, Lison D, and Huaux F. The role of pro- and anti-inflammatory responses in silica-induced lung fibrosis. *Respiratory research.* 2005; 6(112.
13. Spees J L, Pociask D A, Sullivan D E, Whitney M J, Lasky J A, Prockop D J, and Brody A R. Engraftment of bone marrow progenitor cells in a rat model of asbestos-induced pulmonary fibrosis. *American journal of respiratory and critical care medicine.* 2007; 176(4):385-94.
14. Devaney J, Horie S, Masterson C, Elliman S, and Barry F. Human mesenchymal stromal cells decrease the severity of acute lung injury induced by *E. coli* in the rat. *Thorax.* 2015.
15. Oikonomou N, Thanasopoulou A, Tzouvelekis A, Harokopos V, Paparountas T, Nikitopoulou I, Witke W, Karameris A, Kotanidou A, Bouros D, et al. Gelsolin expression is necessary for the development of modelled pulmonary inflammation and fibrosis. *Thorax.* 2009; 64(6):467-75.
16. Zhou Y, Schneider D J, Morschl E, Song L, Pedroza M, Karmouty-Quintana H, Le T, Sun C X, and Blackburn M R. Distinct roles for the A2B adenosine receptor in acute and chronic stages of bleomycin-induced lung injury. *Journal of immunology.* 2011; 186(2):1097-106.
17. Yoshizaki A, Iwata Y, Komura K, Ogawa F, Hara T, Muroi E, Takenaka M, Shimizu K, Hasegawa M, Fujimoto M, et al. CD19 regulates skin and lung fibrosis via Toll-like receptor signaling in a model of bleomycin-induced scleroderma. *The American journal of pathology.* 2008; 172(6):1650-63.
18. Latta V D, Cecchettini A, Ry S D, and Moralesa M. Bleomycin in the setting of lung fibrosis induction: From biological mechanisms to counteractions. *Pharmacological research.* 2015; 97(122-30.
19. Robbe A, Tassin A, Carpentier J, Decleves A E, Mekinda Ngono Z L, Nonclercq D, and Legrand A. Intratracheal Bleomycin Aerosolization: The Best Route of Administration for a Scalable and Homogeneous Pulmonary Fibrosis Rat Model?*BioMed research international.* 2015; 2015 (198418.
20. Tashiro J, Elliot S J, Gerth D J, Xia X, Pereira-Simon S, Choi R, Catanuto P, Shahzeidi S, Toonkel R L, Shah R H, et al. Therapeutic benefits of young, but not old, adipose-derived mesenchymal stem cells in a chronic mouse model of bleomycin-induced pulmonary fibrosis. *Translational research: the journal of laboratory and clinical medicine.* 2015; 166(6):554-67.

21. Dong L H, Jiang Y Y, Liu Y J, Cui S, Xia C C, Qu C, Jiang X, Qu Y Q, Chang P Y, and Liu F. The anti-fibrotic effects of mesenchymal stem cells on irradiated lungs via stimulating endogenous secretion of HGF and PGE2. *Scientific reports*. 2015; 5(8713).
22. How C K, Chien Y, Yang K Y, Shih H C, Juan C C, Yang Y P, Chiou G Y, Huang P I, Chang Y L, Chen L K, et al. Induced pluripotent stem cells mediate the release of interferon gamma-induced protein 10 and alleviate bleomycin-induced lung inflammation and fibrosis. *Shock* 2013; 39(3):261-70.
23. Moodley Y, Atienza D, Manuelpillai U, Samuel C S, Tchongue J, Ilancheran S, Boyd R, and Trounson A. Human umbilical cord mesenchymal stem cells reduce fibrosis of bleomycin-induced lung injury. *The American journal of pathology*. 2009; 175(1):303-13.
24. Zhu H, Xiong Y, Xia Y, Zhang R, Tian D, Wang T, Dai J, Wang L, Yao H, Jiang H, et al. Therapeutic Effects of Human Umbilical Cord-Derived Mesenchymal Stem Cells in Acute Lung Injury Mice. *Scientific reports*. 2017; 7(39889).
25. Yan X, Liu Y, Han Q, Jia M, Liao L, Qi M, and Zhao R C. Injured microenvironment directly guides the differentiation of engrafted Flk-1(+) mesenchymal stem cell in lung. *Exp Hematol*. 2007; 35(9):1466-75.
26. Liang J, Zhang Y, Xie T, Liu N, Chen H, Geng Y, Kurkciyan A, Mena J M, Stripp B R, Jiang D, et al. Hyaluronan and TLR4 promote surfactant-protein-C-positive alveolar progenitor cell renewal and prevent severe pulmonary fibrosis in mice. *Nature medicine*. 2016; 22(11):1285-93.

---

What is claimed is:

1. A method for treating a fibrosis condition of the lung in a subject in need thereof, comprising administering an effective amount of umbilical mesenchymal stem cells (UMSCs) obtained from Wharton's Jelly to the subject, wherein the UMSCs are administered in an amount effective in promoting degradation of fibrotic tissues that have occurred in the lung and/or restoration of lung epithelium of the subject.

2. The method of claim 1, wherein the subject is diagnosed with pulmonary fibrosis.

3. The method of claim 1, wherein the UMSCs are human umbilical mesenchymal stem cells (HUMSCs).

4. The method of claim 1, wherein the method is effective in reducing or alleviating one or more fibrosis conditions of the lung, selected from the group consisting of an elevated level of collagen deposition in the lung, an elevated level of cell infiltration in the lung, an elevated level of lung density and an elevated level of activation of fibroblast in the lung, as compared with a normal level.

5. The method of claim 1, wherein the method is effective in increasing a reduced level of lung volume, a reduced level of lung air space, and/or a reduced level of number of alveoli, as compared with a normal level.

6. The method of claim 1, wherein the method is effective in improving a decreased level of blood oxygen saturation, alleviating an increased level of respiratory rate and/or recovering shrinking of the lung.

7. The method of claim 1, wherein the degradation of fibrotic tissues is caused by activation of matrix metalloproteases in the lung.

8. The method of claim 1, wherein the restoration of lung epithelium includes proliferation of type II alveolar epithelial cells (AEC2s) and transdifferentiation into type I alveolar epithelial cells (AEC1s).

9. The method of claim 1, wherein the UMSCs are administered via injection.

10. A method for promoting degradation of fibrotic tissues in the lung and/or restoration of lung epithelium in a subject in need, comprising administering an effective amount of umbilical mesenchymal stem cells (UMSCs) to the subject, wherein the UMSCs are obtained from Wharton's Jelly.

11. The method of claim 10, wherein the subject is diagnosed with pulmonary fibrosis.

12. The method of claim 10, wherein the UMSCs are human umbilical mesenchymal stem cells (HUMSCs).

13. The method of claim 10, wherein the method is effective in reducing or alleviating one or more fibrosis conditions of the lung, selected from the group consisting of an elevated level of collagen deposition in the lung, an elevated level of cell infiltration in the lung, an elevated level of lung density and an elevated level of activation of fibroblast in the lung, as compared with a normal level.

14. The method of claim 10, wherein the method is effective in increasing a reduced level of lung volume, a reduced level of lung air space, and/or a reduced level of number of alveoli, as compared with a normal level.

15. The method of claim 10, wherein the method is effective in improving a decreased level of blood oxygen saturation, alleviating an increased level of respiratory rate and/or recovering shrinking of the lung.

16. The method of claim 10, wherein the degradation of fibrotic tissues is caused by activation of matrix metalloproteases in the lung.

17. The method of claim 10, wherein the restoration of lung epithelium includes proliferation of type II alveolar epithelial cells (AEC2s) and transdifferentiation into type I alveolar epithelial cells (AEC1s).

18. The method of claim 10, wherein the UMSCs are administered via injection.

* * * * *